United States Patent
Ábrahám et al.

(10) Patent No.: US 12,326,618 B2
(45) Date of Patent: Jun. 10, 2025

(54) METHOD OF DESIGNING A COLOUR FILTER FOR MODIFYING HUMAN COLOUR VISION, SUCH COLOUR FILTER AND COLOUR FILTER SET

(71) Applicant: MEDICONTUR KFT., Zsámbék (HU)

(72) Inventors: György Ábrahám, Budapest (HU); Róbert Tamás Fekete, Budapest (HU); László Kontur, Budapest (HU); Péter Koncsár, Budapest (HU)

(73) Assignee: MEDICONTUR KFT., Zsámbék (HU)

( * ) Notice: Subject to any disclaimer, the term of this patent is extended or adjusted under 35 U.S.C. 154(b) by 562 days.

(21) Appl. No.: 17/765,952

(22) PCT Filed: Oct. 2, 2020

(86) PCT No.: PCT/HU2020/050043
§ 371 (c)(1),
(2) Date: Apr. 1, 2022

(87) PCT Pub. No.: WO2021/064436
PCT Pub. Date: Apr. 8, 2021

(65) Prior Publication Data
US 2022/0365373 A1    Nov. 17, 2022

(30) Foreign Application Priority Data

Oct. 3, 2019  (HU) .................................. P1900344
Dec. 19, 2019 (HU) ................................. 19217955.4

(51) Int. Cl.
*G02B 27/00* (2006.01)
*G02C 7/10* (2006.01)

(52) U.S. Cl.
CPC ......... G02C 7/104 (2013.01); G02B 27/0012 (2013.01); *G02C 2202/06* (2013.01)

(58) Field of Classification Search
USPC .................................................. 359/885–892
See application file for complete search history.

(56) References Cited

U.S. PATENT DOCUMENTS

| | | | | |
|---|---|---|---|---|
| 5,774,202 A | * | 6/1998 | Abraham | G02C 7/00 623/920 |
| 5,801,808 A | * | 9/1998 | Abraham | A61B 3/12 351/221 |
| 7,284,856 B2 | | 10/2007 | Duha et al. | |
| 11,789,293 B2 | * | 10/2023 | Valentine | G02B 5/285 351/159.24 |
| 2014/0233105 A1 | * | 8/2014 | Schmeder | G02C 7/104 359/590 |
| 2019/0219834 A1 | * | 7/2019 | Ace | G02B 5/223 |
| 2022/0003988 A1 | * | 1/2022 | Finlayson | G01J 3/463 |

* cited by examiner

*Primary Examiner* — Darryl J Collins
(74) *Attorney, Agent, or Firm* — Olson & Cepuritis, Ltd.

(57) ABSTRACT

The object of the invention relates to a method of designing a colour filter for modifying human colour vision by defining the spectral transmission function of the colour filter such as to maximise colour discrimination between more than one element, colour sample, of a colour sample set when a targeted human eye, the colour vision of which is to be modified, is viewing the colour sample set with the colour filter, and at the same time such as to minimise the difference between the colour identification of the colour samples by the targeted eye and a reference eye having a reference colour vision. The object of the invention also relates to such a colour filter, such a colour filter set, and the use of such colour filter and a method for modifying human colour vision.

18 Claims, 10 Drawing Sheets

Protos shifted left – protanomaly

Protos shifted onto deuteros – protanopia

Deuteros shifted right – deuteranomaly

Deuteros shifted onto protos – deuteranopia

METHOD OF DESIGNING A COLOUR FILTER FOR MODIFYING HUMAN COLOUR VISION, SUCH COLOUR FILTER AND COLOUR FILTER SET

CROSS-REFERENCE TO RELATED APPLICATION

This application is a U.S. National Stage of PCT/HU2020/050043, filed Oct. 2, 2020, which claims priority to Hungarian Application Nos. P1900344, filed Oct. 3, 2019, and 19217955.4, filed Dec. 19, 2019 each of which is incorporated herein by reference.

The object of the invention relates to a method of designing a colour filter for modifying human colour vision, such colour filter, a set of such colour filters, the use of such colour filter, and a method for modifying human colour vision.

TECHNICAL FIELD

Some of the receptors located in the retina, the cones providing daylight vision, are categorised in three classes depending on their spectral sensitivity. The L-cones are mainly sensitive to the long wavelength (red) part of the spectrum. The M-cones are sensitive to the medium wavelength part of the spectrum and the S-cones to the short wavelength part of the spectrum. The literature calls these L, M and S receptors.

Each cone emits an outgoing signal according to its own spectral sensitivity in response to the light incident on it:

$$L = \int \varphi(\lambda) \cdot l(\lambda) \cdot d(\lambda)$$

$$M = \int \varphi(\lambda) \cdot m(\lambda) \cdot d(\lambda)$$

$$S = \int \varphi(\lambda) \cdot s(\lambda) \cdot d(\lambda)$$

Here $\lambda$ is the wavelength of the light, L, M and S are the outgoing signals of the L-, M- and S-cones, $\varphi(\lambda)$ is the colour stimulus function, i.e. the spectral power distribution of the light incident on the cones, $l(\lambda)$, $m(\lambda)$ and $s(\lambda)$ are the spectral sensitivity functions of the L-, M- and S-cones.

The spectral sensitivity functions of the three types of receptor (L-, M- and S-cones) of the eyes of a human with normal (good) colour vision are shown in FIG. 1 being normalised to 1 by wavelength (see http://www.cvrl.org/cones.htm). Hereinafter the sensitivity functions of the L-, M-, and S-cone colour-sensing receptors are understood to mean curves the maxima of which are at 570 nm, at 542 nm, and at 448 nm respectively.

The sense of colour is produced from the relative values of the stimuli transmitted by the L, M and S colour-sensing receptors compared to each other.

The two most important characteristics of colour vision:
the ability to discriminate colour hue or tone (colour discrimination) is the ability to differentiate between two different colours;
the colour identification ability (colour identification) is the ability with which a person is able to correctly name certain colours or hues.

Both these characteristics are weaker in persons with deficient colour vision than in those with normal colour vision.

Colour vision deficiency is caused by the spectral sensitivity curves of those with deficient colour vision deviating from those of people with normal colour vision to smaller or greater extents in the way illustrated in FIG. 2. Accordingly, the most frequent forms of colour blindness are protanomaly (FIG. 2*a*), protanopia FIG. 2*b*), deuteranomaly (FIG. 2*c*) and deuteranopia (FIG. 2*d*).

FIG. 3 depicts the spectral sensitivity abnormality of protanomaly. As can be seen, the colour sensing problem is caused by the spectral sensitivity of the L-cones being located closer to the spectral sensitivity of the M-cones than in the case of those with normal colour vision. As a consequence of this, due to the effect of a given external stimulus, the difference between the stimuli of the L-cones and M-cones is reduced, and this results in a deterioration of the ability to discriminate colours. In such a case the colour identification ability is also weakened, as the maximum sensitivity of the L-cone receptor is shifted to the left (it will be sensitive to shorter wavelength light).

FIG. 4 depicts the spectral sensitivity of deuteranomaly. In this case the spectral sensitivity of the M-cones is located closer to the spectral sensitivity of the L-cones than in the case of those with normal colour vision. The result is similar to the previous case: the difference between the stimuli of the L-cones and the M-cones is reduced, i.e. in this case also there is a deterioration in the ability to discriminate colours. There is also a deterioration in colour identification, as the maximum sensitivity of the M-cone receptor is shifted to the right (making it sensitive to longer wavelength light).

Colour vision deficiency may be a limiting or even excluding factor in the case of more than 100 occupations. Today good colour vision is required for most work activities. Even now colour vision deficiency is viewed as an incurable disorder as it has a genetic cause, in other words the sensitivity functions of the receptors cannot be changed. However, efforts are being made that are not aimed at improving the sensitivity functions of the receptors, instead they are aimed at attempting to modify the spectrum of the incoming light (using colour filtering), as a result of which improved results may be achieved in spite of the displaced receptor sensitivities. A solution is proposed in patent application number U.S. Pat. No. 5,774,202, according to which the effective or virtual sensitivity of the receptor may be spectrally shifted into the proper direction by using a well-designed colour filter, because the effect of a colour filter may be treated as a detector. To determine the spectral sensitivity of a detector:

$$S_1(\lambda) * \tau(\lambda) = S_2(\lambda)$$

where
$S_1(\lambda)$ is the spectral sensitivity of the detector without the colour filter
$S_2(\lambda)$ is the spectral sensitivity of the detector with the colour filter, and
$\tau(\lambda)$ is the spectral transmission of the colour filter.
From here:

$$\tau(\lambda) = S_2(\lambda) / S_1(\lambda)$$

According to this model the effect of the colour filter is illustrated with the example presented in FIG. 5. For example, the spectral sensitivity function $l^*(\lambda)$ of the L-cone receptors of a person having colour vision deficiency is shifted towards the shorter wavelengths as compared to the spectral sensitivity function $l(\lambda)$ of the same type of receptor of a person with normal colour vision. The filter with spectral transmission $\tau(\lambda)$ shifts the spectral sensitivity function of the receptor to the desired extent, however, due to the effect of the filter sensitivity is temporarily reduced, which can be described with the function $l^{}(\lambda)$. Then again, as a result of the natural adaptation process of the eye sensitivity is restored (white adaptation), and so the sensitivity function l*(λ) obtained in this way is realised with the original maximum in the desired position.

Although the presented system is suitable for restoring the sensitivity of the anomalous receptor, the filter provided in this way does not only influence the receptor that needs correction, it also influences another receptor with a wavelength range close to it. The consequence of this is that the more severe the colour vision deficiency is the weaker the result of this filter design method is.

The examination of the shapes of the ganglion cell signals formed by a known method from the combination and subtraction of the signals from the cones gives a better reference point. This is due to the fact that it is not the primary signals directly originating from the colour-sensing receptors that that are transmitted to the brain, instead it is the signals processed by other cells, i.e. actual sense of colour is based on processed signals. From the point of view of colour vision it is the signal processing performed by the ganglion cells that is decisive. Several types of ganglion cell participate in colour vision, which produce one outgoing channel signal from each of the signals of the L-, M-, and S-cones. There are several models known in the literature for describing the signal processing of the ganglion cells, and these all provide a more precise explanation of colour vision than trichromatic theory, in other words the theory of the combined operation of three photoreceptors of differing sensitivity.

However, the filters according to patent number U.S. Pat. No. 7,284,856, for restoring the shape of the ganglion cells, still do not bring about a solution to or an improvement of the two basic problems of persons with deficient colour vision: bad colour discrimination and incorrect colour identification.

Overall it may be stated that the colour filters presented above primarily provide colour discrimination, but not colour identification, in other words although the person with deficient colour vision is able to discriminate the colour that needs correction from the other colours, he or she does not see them as their real colours. Indeed, in order to provide the experience of colour vision it is not enough to provide colour discrimination, colour identification is also a desirable capability, in other words a person with deficient colour vision whishes to see colours as a person with normal colour vision.

In the light of the above discussion the objective of the invention is a method of designing a colour filter and a colour filter that are free of the disadvantages and deficiencies of the solutions according to the state of the art. The objective of the invention is particularly a method of designing a colour filter and such colour filter for modifying human colour vision that simultaneously improves colour discrimination and colour identification.

The filter design method according to the invention is based on the recognition that in the case of designing the filter the effect of the filter on colour discrimination and its effect on colour identification must both be taken into account. The inventors have recognised that in addition to colour discrimination, colour identification may be ensured to a desired extent if a colour sample set is taken as a basis that consists of a finite number of elements.

It was also recognised that in certain cases it is enough if the discrimination and identification of only certain colour samples are ensured. For example, for a person with red-green colour vision deficiency for safe driving it is enough if they are able to reliably discriminate and identify the red, yellow and green colours used in traffic lights.

It was also recognised that it is also conceivable that the objective is to actually change colour identification of a person with normal colour vision. For example, there are occupations in the case of which it is particularly important to easily and reliably identify certain colours. For example, in the case of the use of certain dashboards and control panels it may be important to recognise the colours of the LED lights and other LED indicators. If these colours actually fall close to each other (such as red and orange), then the correct recognition of the two colours may be tiring during the use of the dashboard for an extended period even for a person with normal colour vision. In this case it would be desirable if the sensing of one of the colours could be changed to a colour that is easier to differentiate, for example, it would be desirable if the operator would have to differentiate the colour yellow instead of orange from the colour red.

The same objective may arise, for example, in the case of the signalling colours used in railway, air and water transport. There may be numerous other fields where it may be useful to more easily differentiate between colours that are close to one another, even by modifying their identification.

It was also recognised by the inventors that the desire of ensuring better colour differentiation while retaining colour identification at the same time may occur even in the case of screens used for entertainment purposes. For example, it could be desirable to modify the sensing of the primary colours of a computer monitor, mobile telephone, tablet, notebook, television screen, etc. even for persons with normal colour vision so that in addition to retaining colour identification, or even making it better, colour discrimination also increases, which would result in a better visual experience.

The above objectives are solved with a method of designing a colour filter for modifying human colour vision by defining the spectral transmission function of the colour filter such as to maximise colour discrimination between the elements of a colour sample set consisting of more than one element when a human eye with given colour vision is viewing the colour sample set with the colour filter, and at the same time such as to minimise the difference between the colour identification of the individual colour samples when viewed by the given eye and when the individual colour samples are viewed without the colour filter by an eye having a given reference colour vision. The eye with the reference colour vision may be an eye with normal colour vision, or an eye with a desired colour vision to be achieved, if, for example, the objective is for the wearer of the colour filter to see certain colour samples of a colour sample set in a colour that differs more from the others.

Maximising the colour discrimination between the colour sample elements does not necessarily mean maximising the colour discrimination between any two colour samples, for example, if the colour samples are quasi monochromatic, then it is sufficient to maximise the colour discrimination between the colour samples in such a way as to achieve enhanced discrimination between consecutive colour samples according to their wavelength.

A particularly preferred embodiment of the filter designing method according to the invention is based on the further recognition that in the case of designing the filter colour points may be determined for a colour sample set consisting of a finite number of colour samples from channel signals calculated on the basis of a ganglion signal processing model, and the filter must be designed for the displacement of these colour points.

On the basis of this recognition a preferred embodiment of the design method is carried out according to claim 3.

In the case of a model based on red-green and blue-yellow opponent channel signals two types of ganglion cells are taken into consideration, one of which provides the red-green channel signal, and the other of which provides the blue-yellow channel signal, on the basis of the following formula, for example:

$$C_{RG}=L-M$$

$$C_{BY}=S-(L+M)$$

where L is the signal (stimulus) provided by the L-cones, M the signal from the M-cones, and S the signal from the S-cones.

Other formulae are also known for calculating the red-green and blue-yellow opponent channel signals, which also provide a better result than directly correcting the sensitivity curves of the cones.

Another preferred embodiment of the invention is based on the recognition that if the colour sample set consists of colour samples taken from the visible light wavelength range at every 1 to 20 nm, preferably at every 5 to 15 nm, even more preferably at every approximately 10 nm, then a colour filter can be produced that ensures appropriate colour vision with respect to practically the entire visible spectrum.

It was also recognised that the colour vision deficiency of persons with colour vision deficiency may be typified, therefore the large majority of persons with colour vision deficiency (approximately 95%) may be successfully covered with, for example, 6 to 8 colour filters according to the invention, preferably even with four such filters, and both a given person's colour discrimination and colour identification may be successfully corrected with one of the elements of the colour filter set.

Further preferred embodiments of the invention are determined in the attached dependent claims.

Further details of the invention will be explained by way of exemplary embodiments with reference to the following figures.

FIG. 1 depicts a graph showing the spectral sensitivity of the L-, M- and S-cone receptors of a person with normal colour vision normalised to 1 as a function of wavelength.

FIGS. 2a-2d present graphs illustrating the displacement of the spectral sensitivity curves corresponding to typical colour vision deficiencies.

Figure 6:
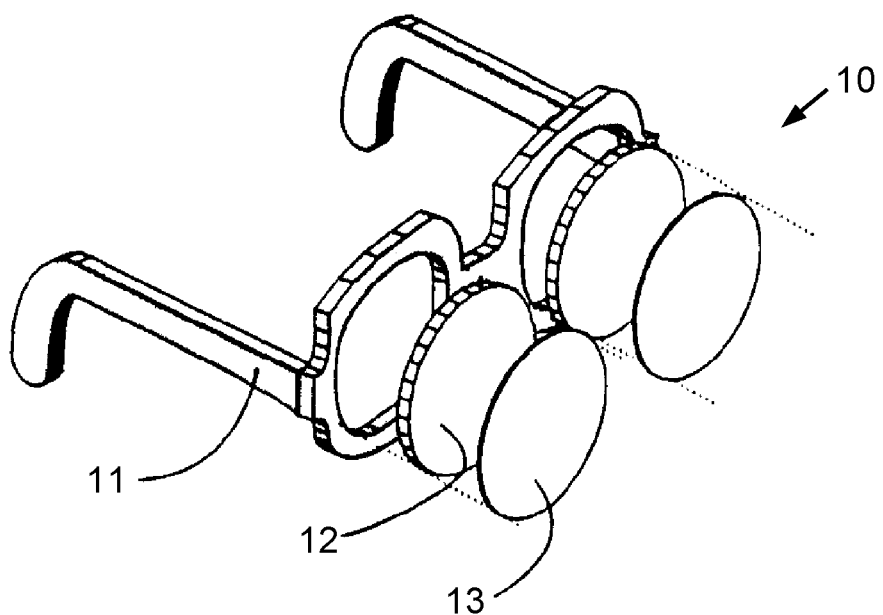
FIG. 6 shows a schematic exploded view of a colour filter according to the invention formed as a spectacle frame.
Figure 6A:
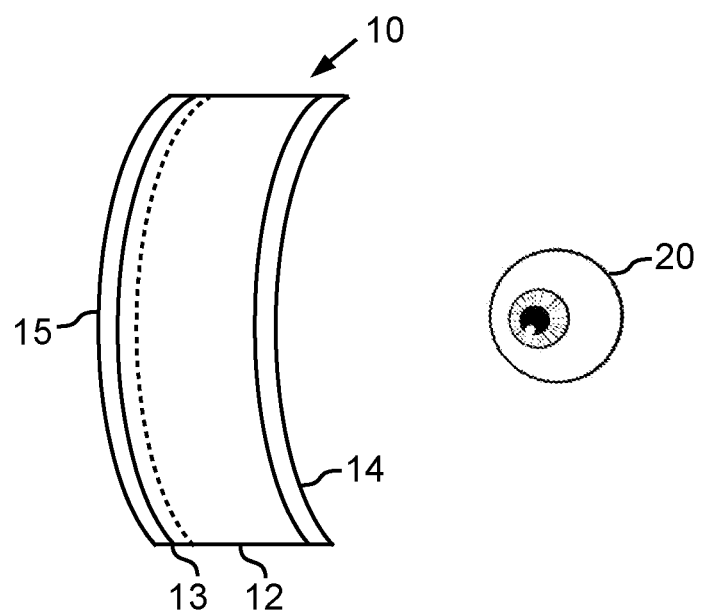
FIG. 6a shows a schematic cross-sectional view of the layer structure of a colour filter according to the invention provided with an absorption layer and UV layer.

FIG. 6 shows a schematic exploded view of a colour filter 10 according to the invention formed as spectacles 10a, where 11 is the spectacle frame, 12 is the carrier lens (corrective or non-corrective), and 13 is the colour filter layer (painted, or a thin layer system, or a combination of these). The colour filter layer 13 is preferably applied to the corrective or non-corrective carrier lens 12 of the spectacles 10a, preferably in the form of optical thin layers or specially composed optically absorbent dye. The colour filter 10 may also be formed by mixing the specially composed optically absorbent dye into the material of the glass or plastic carrier lens using a chemical process, furthermore the colour filter may also be created by mixing the aforementioned technologies. The carrier lens 12 of the spectacles 10a may also have further layers applied to it, for example in a conventional way it may have an absorption layer 14 for reducing reflections, or a UV layer 15 applied to it for filtering UV light, as illustrated schematically in FIG. 6a. The absorption layer 14 is created on the side of the colour filter 10 facing the targeted eye 20, the colour vision of which is to be modified, the UV layer 15 may also be located on the side of the colour filter 10 opposite the targeted eye 20, the colour vision of which is to be modified.

Figure 7:
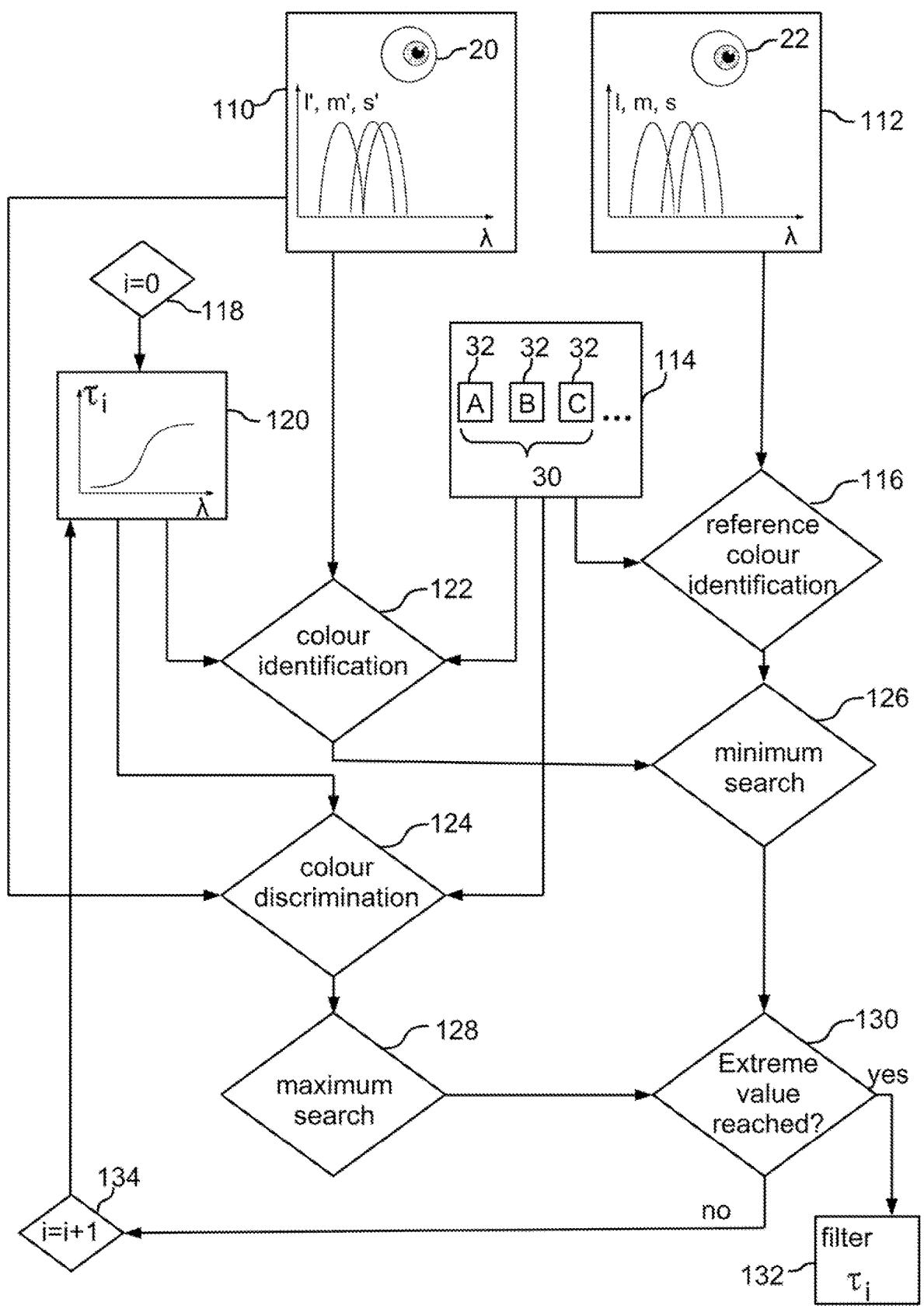
FIG. 7 shows a schematic block diagram of a preferred embodiment of the colour filter design method according to the invention.

A possible embodiment of the process of the design method according to the invention is illustrated in FIG. 7. The reference signs of the steps do not necessarily represent order of sequence; steps that are not necessarily built on one another may follow each other in an order that differs to that given here. The spectral transmission function $\tau(\lambda)$ of the searched for colour filter 10 is designed for a human eye 20 with given colour vision, the L-, M- and S-cone colour-sensing receptors of which may be characterised with the sensitivity functions $l'(\lambda)$, $m'(\lambda)$ and $s'(\lambda)$. The colour filter 10 is designed for a colour sample set 30 consisting of several, but a finite number of colour samples 32 by taking into account how an eye 22 with a reference colour vision sees the individual colour samples 32 without the colour filter 10. The reference colour vision of the eye 22 may be characterised with the sensitivity functions $l(\lambda)$, $m(\lambda)$ and $s(\lambda)$. Accordingly, during the design method the targeted eye 20 is determined in step 110, for example by providing the sensitivity functions l'($\lambda$), m'($\lambda$) and s'($\lambda$) of its L-, M- and S-cone colour-sensing receptors. In the case of a colour filter 10 designed for a concrete patient these sensitivity functions may be determined in a known way. If the task is to modify the colour vision of an eye 20 with normal vision, then the starting point may be the values of the sensitivity functions found in the literature. The starting point in the case of designing a colour filter 10 for correcting typical deficient colour vision may be the sensitivity functions of the colour sensing receptors of a typical person with deficient colour vision.

The reference eye 22 is determined in step 112, which may be carried out by providing the sensitivity functions l($\lambda$), m($\lambda$) and s($\lambda$) of its L-, M- and S-cone colour-sensing receptors, but the desired colour vision may be described in other ways, as will be seen in the following. The reference eye 22 may be an eye with normal colour vision if the targeted eye 20 has deficient colour vision, and the purpose is to correct defective colour vision. In other cases the reference eye 22 may be an eye the colour vision of which is to be achieved.

In step 114 the colour samples 32 of the colour sample set 30 are determined 32, for example, with their spectral luminance distribution under given ambient lighting, or without lighting in the case of self-illuminating colour samples 32 (e.g. LED lights).

The spectral transmission function $\tau(\lambda)$ is determined so that the colour filter 10 maximises the colour discrimination between the individual colour samples 32 when the targeted human eye 20 sees the colour sample set 30, and simultaneously minimises the difference between the colour identification occurring when the given reference eye 22 sees the corresponding colour samples 32. In other words, not only is differentiation between the colour samples 32 of the colour sample set 30 enabled (as with the solutions according to the state of the art), attention is also paid to what colour the targeted human eye 20 sees the individual colour samples 32 as.

The method involves searching for extreme values, which only represents maximisation of colour discrimination and minimisation of the colour identification difference as compared to a reference colour identification with respect to each other, however, taken separately it does not mean maximisation and minimisation because the parameters are not independent of each other. Due to this, preferably extreme value search algorithms are used in which both factors (colour discrimination and colour identification) appear at the same time.

Extreme value searching may be performed using the iteration presented in FIG. 7.

In step 116 the reference colour identification of the reference eye 22 is determined for each and every colour sample 32. This may also take place through simulation.

In step 118 the current iteration serial number i=0 is given (naturally the iteration may be started at another serial number) then in step 120 the spectral transmission function $\tau_{i=0}(\lambda)$ of the colour sample belonging to iteration i is given, which, when the iteration is started, is the spectral transmission function $\tau_0(\lambda)$ corresponding to an initial colour filter. If the vision of the eye 20 without the colour filter 10 is also to be determined then the spectral transmission function $\tau_0(\lambda)$ may be selected as the constant function with the value 1.

According to experience the iteration may be started at practically any function $\tau_0(\lambda)$, all that may happen is that more iterations are required to find the extreme value.

Following this, in step 122 the colour identification resulting from the optical system comprising the eye 20 and the colour filter 10 described by the spectral transmission function $\tau_{i=0}(\lambda)$ is determined for the individual colour samples 32, and in step 124 the colour discrimination is determined that the optical system provides between the individual colour samples 32. If the colour samples 32 can be placed in order according to their wavelength, then in the case of a possible embodiment of the method only the colour discrimination between colour samples 32 that are consecutive according to wavelength is determined, which, in the case of a large number of colour samples 32, significantly reduces the calculation demand of the design method.

On the basis of the values obtained, in step 126 the difference between the reference colour identification and the colour identifications obtained with the initial colour filter is calculated for each colour sample 32, and the differences are processed with an algorithm that searches for the minimum. Similarly, in step 128 the values obtained for colour discrimination are processed with an algorithm searching for the maximum. Preferably the minimum-searching algorithm used in step 126 and the maximum-searching algorithm used in step 128 are realised within the scope of a single extreme-value-searching algorithm, in other words, these steps are only separated in FIG. 7 for the sake of better illustration.

Many types of extreme-value-searching algorithm are known to a person skilled in the art. According to the inventors experience the gradient descent, the Newton method and the genetic algorithm are all suitable for performing the extreme-value-searching method according to the invention.

Following this, in step 130 it is decided whether the combined optimum for the minimum search and maximum search has been reached, in other words the combined extreme value. As a consequence of the nature of numerical extreme-value-searching algorithms, the extreme values are only approximations, but in the context of the present invention the result that the numerical algorithm provides as result is deemed to be the extreme value.

Preferably, during the combined minimum and maximum search the colour discrimination values and the colour identification difference values are taken into consideration by applying weighting factors corresponding to the importance of the two criteria as compared to each other. Such importance as compared to each other may be, for example, that the colour discrimination between two or more colour samples 32 is realised even to the detriment of the colour identification as compared to the reference colour identification. In the case of another example, weighting factors are applied in order to ensure that true colour identification of certain colour samples 32 is more important than that of other colour samples 32, in other words a greater deviation as compared to the reference colour identification is permitted in the case of certain colour samples 32 (these are taken into account with a lower weighting factor when calculating the extreme values).

In case it is found in step 130 that the extreme-value-searching algorithm has reached the optimum (extreme value), then in step 132 it is determined that the spectral transmission function $\tau(\lambda)$ of the searched colour filter 10 is equal to the spectral transmission function $\tau_i(\lambda)$ used in iteration i, in other words the spectral transmission function $\tau(\lambda)$ describing the colour filter 10 has been designed, which, following this, may then be manufactured in a known way.

In the case that it is found in step 130 that that the extreme-value-searching algorithm has not yet reached its optimum, the iteration is continued, in other words, in step 134 the iteration serial number is increased stepwise, preferably according to the formula i=i+1, and preferably using the extreme-value-searching algorithm and taking the result of the previous iteration into account a new spectral transmission function $\tau_i(\lambda)$ is provided, with which steps 122 to 130 are repeated.

Figure 8:
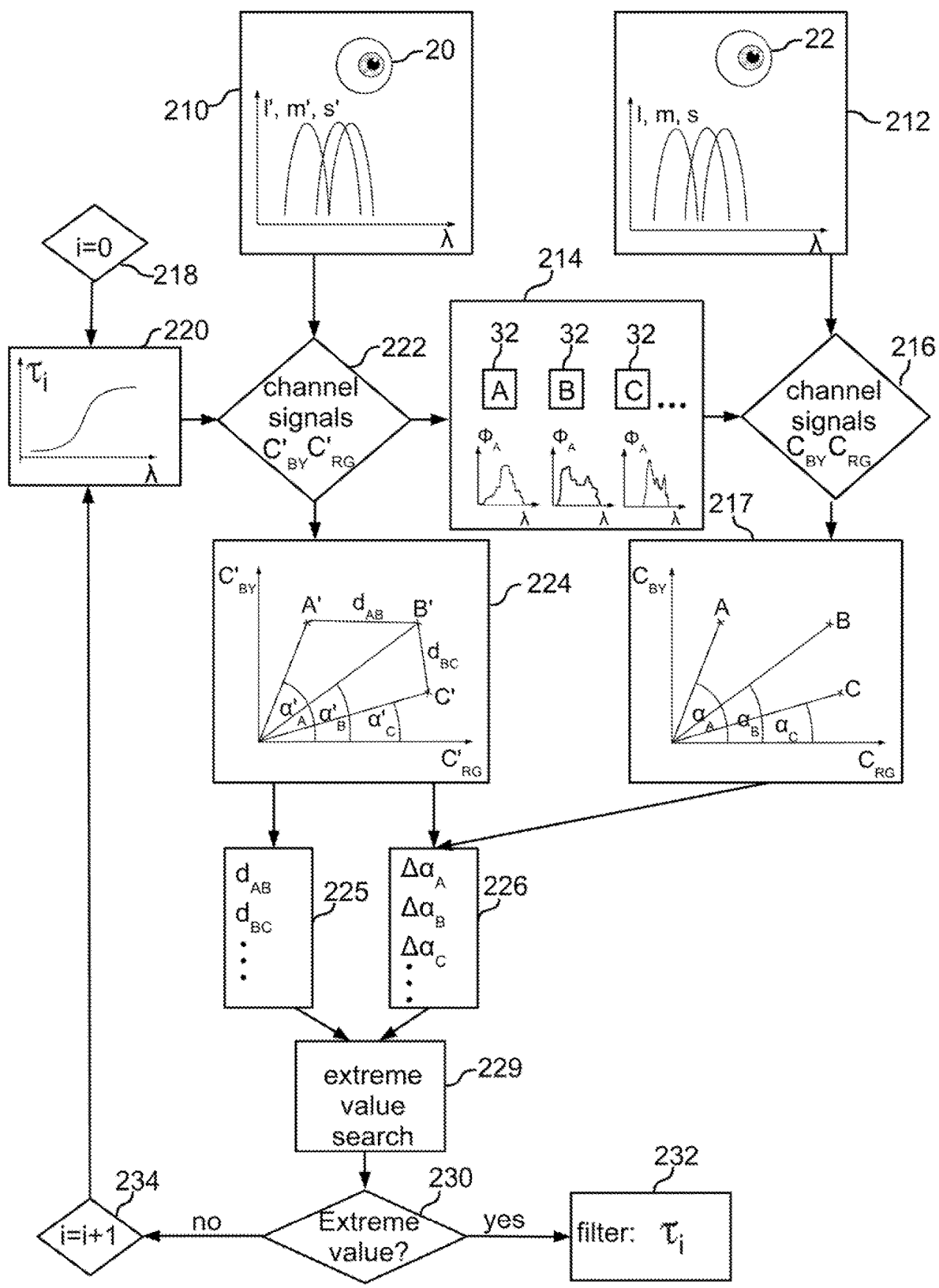
FIG. 8 shows a schematic block diagram of a preferred embodiment of the colour filter design method according to the invention.

In the case of a particularly preferred embodiment of the design method according to the invention colour discrimination maximising and minimising the colour identification difference as compared to a reference colour identification is performed using channel signals describing human colour vision, as illustrated in the flow diagram according to FIG. 8. During the design method, in step 210, the spectral sensitivity functions $l'(\lambda)$, $m'(\lambda)$ and $s'(\lambda)$ belonging to the L-, M-, and S-cone receptors of the targeted human eye are determined similarly to that described previously. In step 212 the reference eye is determined, which may take place by providing the spectral sensitivity functions $l(\lambda)$, $m(\lambda)$ and $s(\lambda)$ of the L-, M-, and S-cone receptors.

In step 214 the spectral luminance distributions $\pi_A(\lambda)$, $\phi_B(\lambda)$, $\phi_C(\lambda)$, etc. of the colour samples 32 of the colour sample set 30 are provided for given ambient lighting, or without it in the case of self-illuminating colour samples 32 (e.g. LED lamps).

In the case of the present embodiment the maximising of the colour discrimination and, simultaneously, the minimising of the differences between the colour identification occurring when the individual colour samples 32 are seen and the colour identification occurring when the given reference eye 22 sees the corresponding colour samples 32 without colour filter 10 is carried out using the channel signals describing the colour vision.

For this, in step 216 the opponent channel signals describing human colour vision on the basis of a selected literature model are determined for the reference eye 22, then these opponent channel signals are used to provide colour points A, B, C, etc. The channel signals may be determined from the sensitivity functions $l(\lambda)$, $m(\lambda)$ and $s(\lambda)$ of the L-, M- and S-cone receptors of the reference eye 22, however, the channel signals may be provided in absence of any sensitivity functions as well. The latter is particularly preferred in case the reference eye 22 is not an eye with normal colour vision, instead it is intentionally an eye with modified colour vision (for example, in the interest of allowing certain colours to be better discriminated from each other while carrying out work or a free-time activity, for example the colours green and yellow are to be better differentiated by using a reference eye 20, which perceives green as turquoise), whereby the receptor spectral sensitivity functions of such a reference eye 22 are not precisely known. In such a case the reference eye 22 is an eye that sees the colour samples 32 according to the colours to be achieved (for example, it sees the wavelength corresponding to the colour green as a person with normal colour vision sees the colour turquoise, while it sees the other colours as a person with normal colour vision sees them), and the reference spectral sensitivity functions $l(\lambda)$, $m(\lambda)$ and $s(\lambda)$ are the sensitivity functions of the L-, M- and S-cone receptors of such an eye. As it is not necessarily certain that these reference spectral sensitivity functions $l(\lambda)$, $m(\lambda)$ and $s(\lambda)$ can be provided, in this case the channel signals are not calculated, instead they are provided in accordance with the colour vision to be achieved. Remaining with the above example, the channel signals for each colour sample 32 are provided as follows: for a green coloured colour sample 32 the channel signals of an eye with normal colour vision obtained for a turquoise coloured colour sample 32 are provided, while for all other colour samples 32 the channel signals of an eye with normal colour vision obtained for these other colour samples 32 are provided. With this, without knowing the reference spectral sensitivity functions $l(\lambda)$, $m(\lambda)$ and $s(\lambda)$, it can be ensured that the reference eye 20 sees the colour green as being turquoise and sees the other colours as an eye with normal colour vision does.

In the case of the present example red-green and blue-yellow opponent channel signals ($C_{RG}$, $C_{BY}$) are used, and the opponent channel signals are calculated on the basis of the following formulae:

$$C_{RG} = L - M$$

$$C_{BY} = S - (L + M)$$

where L is the incoming signal (in other words the detected light intensity) of the L-cones, M is the signal from the M-cones, and S is the signal from the S-cones. Naturally other channel signals accepted in the literature may be used instead of the above formulae.

Figure 8A:
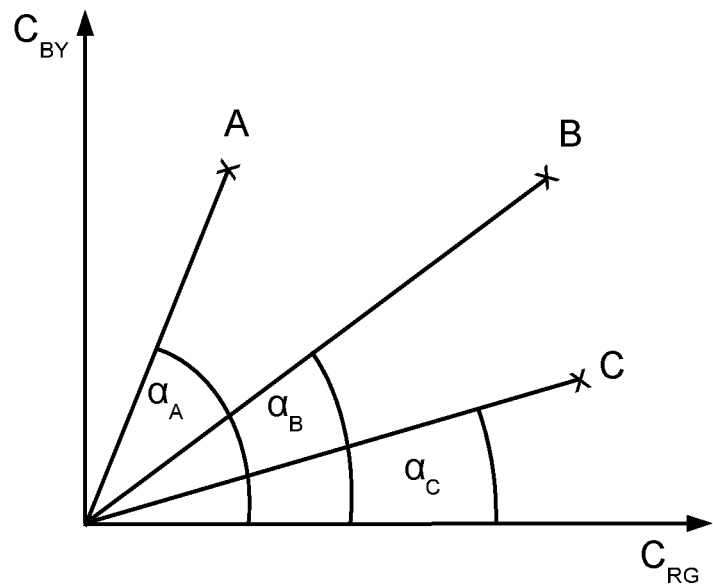
FIG. 8a shows the colour points corresponding to three colour samples sensed by a reference eye plotted in a coordinate system formed by the red-green and blue-yellow opponent channel signals as coordinate axes.

In step 217 the reference hue angles $\alpha_A$, $\alpha_B$, $\alpha_C$, etc. relating to the individual colour samples 32 are determined from the channel signals, which in the case of two channel signals correspond to the angle between the straight line drawn from the origin to the colour point and one of the axes in a 2-dimensional right-angled coordinate system with the channels as axes, as illustrated separately in FIG. 8a. Depicting the colour points in a right-angled coordinate system with the channels as axes is not necessary to determine the hue angles. For example, if red-green and blue-yellow opponent channel signals ($C_{RG}$, $C_{BY}$) are used as the channel signals then the hue angles are determined with the relationship $$\alpha = \text{arc}tg\frac{y}{x}$$

where the variable x corresponds to one of the channel signal values $C_{RG}$, $C_{BY}$ and the variable y corresponds to the other one of the channel signal values $C_{RG}$, $C_{BY}$. As in the following only hue angle differences are required there is no significance to which channel is treated as the x axis, i.e. which axis the hue angle is measured from.

Figure 9A:
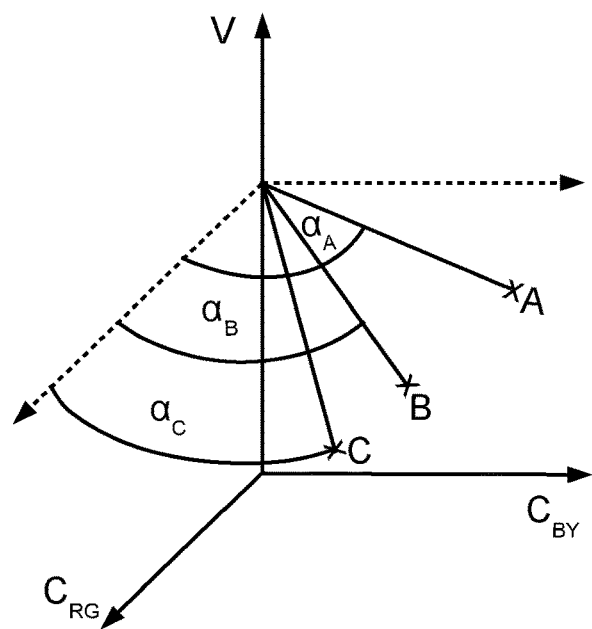
FIG. 9a shows the colour points corresponding to the three colour samples according to FIG. 8a plotted in a coordinate system formed by the red-green and blue-yellow opponent channel signals as well as the channel signal corresponding to brightness as coordinate axes.
Figure 9B:
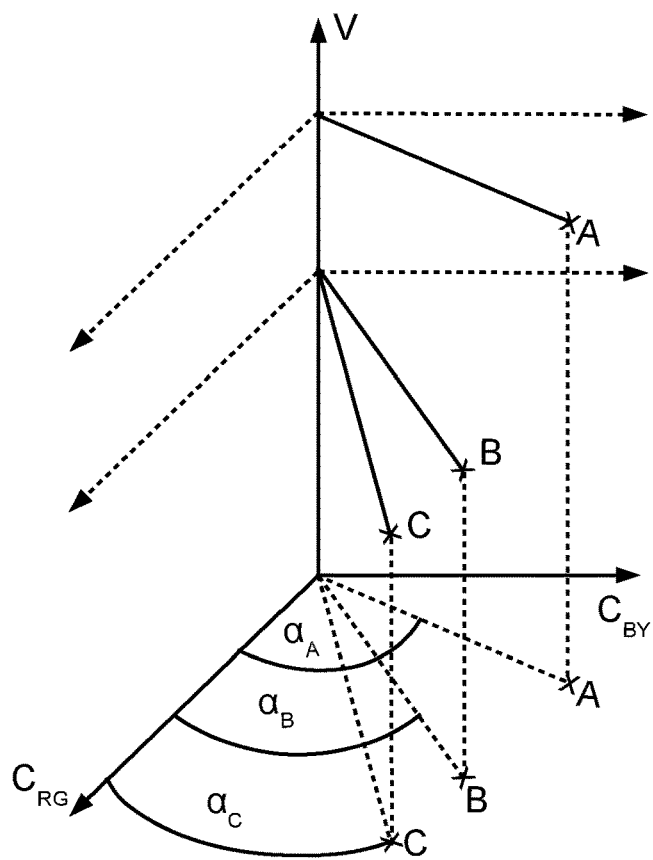
FIG. 9b shows the example according to FIG. 8a with the difference that the brightness of one of the colour samples deviates from that of the other two colour samples.

It should be noted that the coordinate system may also contain a third axis, on which brightness is measured—a third ganglion cell is responsible for the sensing of this, which, however, does not participate in colour vision. If the brightness of each of the colour samples 32 is the same, or they are viewed in the same ambient lighting, then the brightness axis has no significance, as all the colour points fall in a plane perpendicular to the brightness axis, as illustrated in FIG. 9a. If, however, the brightness of each of the colour samples is not the same (because, for example, colour samples 32 that shine at different levels of brightness are used), then the colour points A, B, C do not fall in the same plane, as illustrated by FIG. 9b, where the colour sample 32 corresponding to the colour point A is brighter than the colour samples 32 corresponding to the colour points B and C. In this case the hue angles $\alpha_A$, $\alpha_B$, $\alpha_C$, are determined by projecting the spatial colour points A, B, C onto the plane determined by the axes $C_{RG}$, $C_{BY}$, and the distances of the colour point are determined as spatial distances.

It should also be noted that the distance of the projection of each of the colour points measured from the origin gives the saturation of the viewed colour.

In the case of the design method according to FIG. 8, in step 218 the current iteration serial number i=0 is provided (naturally the iteration may be started at another serial number), then in step 220 the spectral transmission function $\tau_i(\lambda)$ of the colour sample belonging to iteration i is provided, which, when the iteration is started, is the spectral transmission function $\tau_0(\lambda)$ corresponding to an initial colour filter. It is noted that the iteration may be started at practically any function, all that may happen is that more iterations are required to find the optimum.

Following this, in step 222, the channel signals $C'_{RG}$, $C'_{BY}$ of the eye 20 modified by the initial colour filter with spectral transmission $T_0(\lambda)$ are calculated from the spectral sensitivity functions $l'(\lambda)$, $m'(\lambda)$ and $s'(\lambda)$ of the L-, M- and S-cone receptors for each colour sample 32, then in step 224 the modified channel signals $C'_{RG}$, $C'_{BY}$ are used to determine for each colour sample 32 modified colour points A', B', C', etc., and then the modified hue angles $\alpha'_A$, $\alpha'_B$ and $\alpha'_C$, are calculated in the way described above.

In FIG. 8, in step 224 for the sake of illustration the modified colour points A', B', C', etc. have also been depicted in a right-angled coordinate system formed by the channels as axes, this, however, is not necessary in order to determine the hue angles or the colour discrimination values.

In step 225 at least the distances of the modified colour points A', B', C' are determined with respect to each other, which modified colour points A', B', C' relate to the colour samples 32 that are consecutive according to wavelength. This may be done, for example, from the channel signals $C'_{RG}$, $C'_{BY}$ forming the coordinates of the colour points A', B', C'. In step 226 the hue angle differences $\Delta\alpha_A$, $\Delta\alpha_B$ and $\Delta\alpha_C$ between the hue angles of the reference colour points A, B, C and the corresponding modified colour points A', B', C' are determined.

Figure 8B:
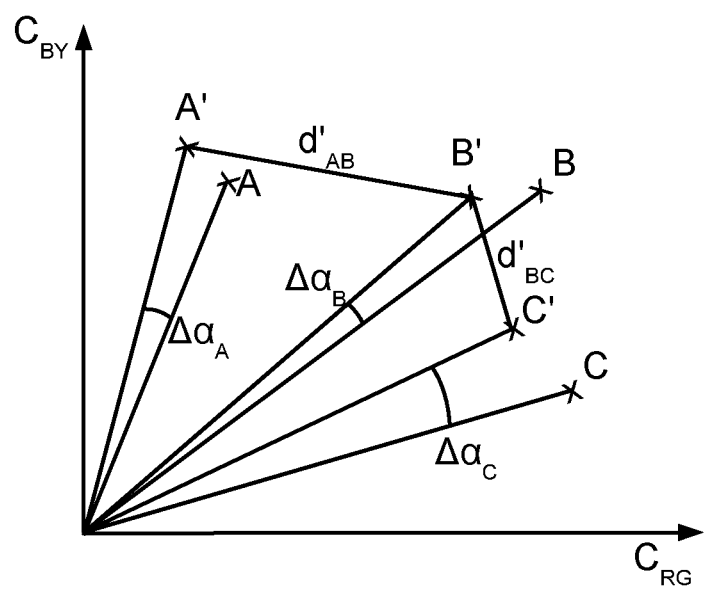
FIG. 8b shows the colour points corresponding to the three colour samples according to FIG. 8a seen with a reference eye and with a targeted human eye, the colour vision of which is to be modified, and which is provided with a colour filter, the colour points being plotted in a right-angled coordinate system formed by the red-green and blue-yellow opponent channel signals as coordinate axes.

For the sake of illustration in FIG. 8b the reference colour points A, B, C have been shown in a common coordinate system with the modified colour points A', B', C' obtained with the initial colour filter. FIG. 8b also shows the distances $d'_{AB}$, $d'_{BC}$ of those modified colour points A', B', C', which relate to the colour samples 32 that are consecutive according to wavelength, as well as the hue angle differences $\Delta\alpha_A$, $\Delta\alpha_B$ and $\Delta\alpha_C$ between the hue angles of the reference colour points A, B, C and of the corresponding modified colour points A', B', C'. It should be noted that in order to determine the hue angle differences $\Delta\alpha_A$, $\Delta\alpha_B$ and $\Delta\alpha_C$ between the reference colour points A, B, C and the corresponding modified colour points A', B', C' it is not necessary to actually calculate the reference hue angles $\alpha_A$, $\alpha_B$, $\alpha_C$ and the modified hue angles $\alpha'_A$, $\alpha'_B$, $\alpha'_C$, as these are angles defined by the channel signal pairs $C_{RG}$, $C_{BY}$ and $C'_{RG}$, $C'_{BY}$ as coordinate pairs, and the angle differences between these may be calculated without determining the angles from the channel signal pairs $C_{RG}$, $C_{BY}$ and $C'_{RG}$, $C'_{BY}$.

Following this, in step 229 an extreme value searching algorithm is used to determine whether at least the distances between the modified colour points obtained in step 225 relating to wavelength-consecutive colour samples 32 are the greatest possible distances and at the same time the hue angle differences obtained in step 226 are the smallest possible angles, and in step 230 it is determined whether the extreme value searching algorithm has reached the extreme value. If so, then in step 232 it is determined that the spectral transmission function $\tau(\lambda)$ of the searched colour filter 10 is equal to the spectral transmission function $\tau_i(\lambda)$ used in iteration i, meaning that the spectral transmission function $\tau(\lambda)$ describing the desired colour filter 10 has been designed, which, following this, may be manufactured in a known way.

If it is found in step 230 that that the extreme-value-searching algorithm has not yet reached the optimum, the iteration is continued, in other words, in step 234 the iteration serial number is increased stepwise, preferably according to the formula i=i+1, and preferably using the extreme-value-searching algorithm and taking the result of the previous iteration into account a new spectral transmission function $\tau(\lambda)$ is provided, with which steps 222 to 230 are repeated.

It is true in the present case also that the distances between the modified colour points relating to wavelength-consecutive colour samples 32 and/or the angle differences between the modified hue angles of the modified colour points and the reference hue angles of the corresponding reference colour points may also be taken into consideration by applying a given weighting factor, for example, for the purpose of better satisfying a specific purpose.

In the following the design method according to the invention is illustrated by way of specific examples.

EXAMPLE 1

The targeted eye 20 according to example 1 has protanomaly colour vision deficiency, and the spectral sensitivity function $l'(\lambda)$ of its L-cone receptor is shifted by 20 nm in the direction of the shorter wavelength, therefore the maximum value of the spectral sensitivity function of the L-cone receptor is not at 571 nm corresponding to persons with normal colour vision, but at 551 nm, while the maximum values of the spectral sensitivity function $m'(\lambda)$ of the M-cone receptors and the spectral sensitivity function $s'(\lambda)$ of the S-cone receptors correspond to the 542 nm and the 448 nm of an eye with normal colour vision.

In the present case the goal is to restore the deficient colour vision of a person with protanomaly colour vision deficiency, therefore the reference eye 22 will be an eye 22 with normal colour vision.

According to the example the colour sample set 30 consisting of a finite number of colour samples 32 is the spectral luminance distribution $\phi_{red}(\lambda)$, $\phi_{green}(\lambda)$, $\phi_{yellow}(\lambda)$ of the red, green and yellow lights of a set of traffic lights, which may be determined in a known way, for example using a spectroradiometer.

It should be pointed out here that the individual colour samples 32 are not necessarily monochromatic colours characterised by a single wavelength, instead each may be a mixture of light of several wavelengths, in other words a spectrum. In the present case the colour samples 32 themselves radiate the multiple-wavelength light, therefore sensing the colour samples 32 may be treated as being substantially independent of the external lighting conditions. If a colour sample set 30 is used the colour samples 32 of which do not themselves radiate light, in other words the observer identifies their colours with the colour of the reflected light from the external light source, then it is preferred to apply external lighting characteristics when determining the spectral luminance distribution of the colour samples 32 which characteristics are typical for the environmental conditions in which the colour filter 10 would be used. In this case the spectral luminance distribution may be recorded using a reflection spectrophotometer containing such a light source, for example.

In the case of the present example red-green and blue-yellow opponent channel signals ($C_{RG}$, $C_{BY}$) are used. Accordingly, for example, the opponent channel signals $C_{RG}$ (red), $C_{BY}$ (red) created by the ganglion cells in response to the effect of the stimuli created in the cone receptors of the eye with normal colour vision in the case of viewing the red coloured traffic light as the colour sample 32 can be determined as follows:

$$L(red) = \int_{380}^{780} \phi_{red}(\lambda) l(\lambda) l(\lambda) \phi(\lambda) d\lambda$$

$$M(red) = \int_{380}^{780} \phi_{red}(\lambda) m(\lambda) \lambda d\lambda$$

$$S(red) = \int_{380}^{780} \phi_{red}(\lambda) s(\lambda) \lambda d\lambda,$$

where $l(\lambda)$, $m(\lambda)$ and $s(\lambda)$ indicate the spectral sensitivity functions of the L-, M- and S-cone receptors of an eye 22 with normal colour vision.

From this the opponent channel signal may be obtained with the following formulae:

$$C_{RG}(red) = L(red) - M(red)$$

$$C_{BY}(red) = S(red) - [L(red) + M(red)].$$

The same opponent channel signals are also determined for the green and yellow traffic lights, as colour samples 32 in the case of the eye 22 with normal colour vision:

$$C_{RG}(green), C_{BY}(green)$$

$$C_{RG}(yellow), C_{BY}(yellow)$$

The opponent channel signals obtained in this way are viewed as coordinate pairs for each colour sample 32, which pairs each specify a colour point in a right-angled coordinate system formed by the perpendicular axes $C_{RG}$-$C_{BY}$ similarly to FIG. 8b, which colour points are denoted accordingly with the letters R, G and Y for the red, green and yellow traffic lights as colour samples 32. In other words R marks the colour point with coordinates [$C_{RG}$ (red), $C_{BY}$ (red)], G marks the colour point with coordinates [$C_{RG}$ (green), $C_{BY}$ (green)], and Y denotes the colour point with coordinates [$C_{RG}$ (yellow), $C_{BY}$ (yellow)].

In the second step the angles between a straight line linking the individual colour points R, G, Y in the case of the eye 22 with normal colour vision to the origin of the coordinate system and the horizontal $C_{RG}$ axis are determined, in other words the hue angles, using the relationship $$\alpha = \arctg \frac{C_{BY}}{C_{RG}}$$

for each colour point R, G, Y belonging to each colour sample 32.

In this way the angles $\alpha(red)$, $\alpha(green)$, $\alpha(yellow)$ are provided.

In the third step modified opponent channel signal pairs [$C'_{RG}$ (red), $C'_{BY}$ (red)], [$C'_{RG}$ (green), $C'_{BY}$ (green)], [$C'_{RG}$ (yellow), $C'_{BY}$ (yellow)] of the targeted eye 20 relating to the individual traffic light colours are calculated in the case of observation through an initial colour filter that may be described with an initial spectral transmission function, which channel signal pairs determine the colour points denoted by R', G' and Y', respectively. The receptor signals sensed through the initial colour filter and modified by it are calculated as:

$$L'(red) = \int_{380}^{780} \phi_{red}(\lambda) l'(\lambda) \tau_0(\lambda) d\lambda$$

$$M'(red) = \int_{380}^{780} \phi_{red}(\lambda) m'(\lambda) \tau_0(\lambda) d\lambda$$

$$S'(red) = \int_{380}^{780} \phi_{red}(\lambda) s'(\lambda) \tau_0(\lambda) d\lambda$$

The opponent channel signals are obtained from this in the way described above.

Following this the distances measured between the colour points R', G' and Y' defined by the opponent channel signal pairs are determined within the coordinate system.

For the red-green lights $$d_{RG} = \sqrt{[C'_{BY}(red) - C'_{BY}(green)]^2 + [C'_{RG}(red) - C'_{RG}(green)]^2},$$

for the red-yellow lights $$d_{RY} = \sqrt{[C'_{BY}(red) - C'_{BY}(yellow)]^2 + [C'_{RG}(red) - C'_{RG}(yellow)]^2},$$

and for the yellow-green lights $$d_{YG} = \sqrt{[C'_{BY}(yellow) - C'_{BY}(green)]^2 + [C'_{RG}(yellow) - C'_{RG}(green)]^2},$$

The hue angles $\alpha'(red)$, $\alpha'(green)$, $\alpha'(yellow)$ are calculated from the modified opponent channel signal pairs using the relationship:

$$\alpha = \arctg \frac{C'_{BY}}{C'_{RG}}$$

for each colour point R', G', Y' belonging to each colour sample 32.

Following this the differences of the hue angles relating to the individual traffic lights sensed through the colour filter and sensed by the eye 22 with normal colour vision are also determined:

$$\Delta\alpha(red) = \alpha'(red) - \alpha(red)$$

$$\Delta\alpha(green) = \alpha'(green) - \alpha(green)$$

$$\Delta\alpha(yellow) = \alpha'(yellow) - \alpha(yellow)$$

In the fourth step the value of the initial function $\tau_0(\lambda)$ is changed stepwise, for example using the known extreme-value-searching method, until the maximum distance $d_{RG}$, $d_{RY}$ and $d_{YG}$ values and the minimum angle difference $\Delta\alpha(red)$, $\Delta\alpha(green)$, $\Delta\alpha(yellow)$ values are achieved. The present design method will yield the colour filter 10 with spectral transmission $\tau(\lambda)$ corresponding to the extreme value, which colour filter 10 may then be manufactured using known methods.

EXAMPLE 2

Example 2 differs from example 1 in that the colour sample set 30 consists of the signalling colours used expressly in railway transport and/or air transport and/or water transport, which may be the colours of light sources as well as the colours of signalling discs or signalling boards.

EXAMPLE 3

Example 3 differs from example 1 in that the colour sample set 30 consisting of several samples consists of the colours of given LED lights of a dashboard or control panel, and the goal is to modify normal colour vision so that the individual LED colours are easier to discriminate, even at the cost of showing the colour of a particular LED as a substantially different colour. For example, the colours of the LED seen as red and orange without the colour filter are modified using the colour filter 10 according to the invention so that the red LED is still seen as red while the orange LED is seen as yellow by a person with normal colour vision.

In this case the first colour sample 32 is the light of the red coloured LED, and the second colour sample 32 is the light of the orange coloured LED, which can be described with the spectral luminescence distributions $\phi_{red}(\lambda)$, $\phi_{orange}(\lambda)$, accordingly.

The targeted eye 20 to be modified is an eye with normal colour vision, because in this example work spectacles are being designed for persons with normal colour vision. The spectral sensitivity functions $l'(\lambda)$, $m'(\lambda)$ and $s'(\lambda)$ of the L-, M- and S-cone receptors of the targeted eye 20 to be modified are the same as the spectral sensitivity curves of the L-, M- and S-cone receptors of an eye with normal colour vision, which, in the present case, are described with the functions $l(\lambda)$, $m(\lambda)$ and $s(\lambda)$.

The spectral sensitivity functions of the L-, M- and S-cone receptors of the reference eye 22 are not known. Instead, a spectral luminance distribution $\phi_{yellow}(\lambda)$ is determined describing the light of a yellow coloured LED because the light of the orange coloured LED is desired to be seen as the light of the yellow LED. The function $\phi_{yellow}(\lambda)$ may correspond to the spectrum of an existing yellow coloured LED light, but it may also be a theoretical function, for example the spectral luminescence distribution of a monochromatic light, that has a non-zero value at a single yellow wavelength (such as at 580 nm).

Following this the opponent channel signal pairs $C_{RG}$ (red), $C_{BY}$ (red), and $C_{RG}$ (orange), $C_{BY}$ (orange) are determined which are created by the ganglion cells when the colour samples 32 are observed. As the intention is for the reference eye 22 to see the colour of the red LED light as an eye with normal colour vision, in order to calculate the channel signals $C_{RG}$ (red), $C_{BY}$ (red) by the above used formulae the spectral sensitivity functions $l(\lambda)$, $m(\lambda)$ and $s(\lambda)$ of an eye with normal colour vision and the spectral luminescence distribution $\phi_{red}(\lambda)$ are used in the following formulae:

$L(red) = \int_{380}^{780} \phi_{red}(\lambda) l(\lambda) d\lambda$ $M(red) = \int_{380}^{780} \phi_{red}(\lambda) m(\lambda) d\lambda$ $S(red) = \int_{380}^{780} \phi_{red}(\lambda) s(\lambda) d\lambda$ From this the opponent channel signals are calculated using the following formulae:

$C_{RG}(red) = L(red) - M(red)$ $C_{BY}(red) = S(red) - [L(red) + M(red)]$.

The objective is to ensure that the targeted eye 20 sees the light of the orange coloured LED as the reference eye 22 would see yellow, in other words those channel signals are sought that an eye 22 with normal colour vision would produce in the case of observing a LED with spectral luminescence $\phi_{yellow}(\lambda)$, which are obtained as follows:

$L(orange) = \int_{380}^{780} \phi_{yellow}(\lambda) l(\lambda) d\lambda$ $M(orange) = \int_{380}^{780} \phi_{yellow}(\lambda) m(\lambda) d\lambda$ $S(orange) = \int_{380}^{780} \phi_{yellow}(\lambda) s(\lambda) d\lambda$, from which the channel signals are:

$C_{RG}(orange) = L(orange) - M(orange)$ $C_{RG}(orange) = S(orange) - [L(orange) + M(orange)]$.

In the second step the hue angles $\alpha$ belonging to the individual channel signal pairs are determined in the case of the reference eye 22 using the relationship $$\alpha = arctg \frac{C_{BY}}{C_{RG}}$$

In this way the hue angles $\alpha(red)$, $\alpha(orange)$ can be calculated.

As the third step the modified channel signal pairs $[C'_{RG}(red), C'_{BY}(red)]$, $[C'_{RG}(orange), C'_{BY}(orange)]$ are calculated, which relate to the individual light colours as seen by the targeted normal colour vision eye 20 in the case of viewing through an initial colour filter described with an arbitrary spectral transmission function $\tau_0(\lambda)$. The receptor signals sensed through the initial colour filter and modified by it are calculated as follows.

For the red LED light, as colour sample 32:

$L(red) = \int_{380}^{780} \phi_{red}(\lambda) l(\lambda) \tau_0(\lambda) d\lambda$ $M(red) = \int_{380}^{780} \phi_{red}(\lambda) m(\lambda) \tau_0(\lambda) d\lambda$ $S(red) = \int_{380}^{780} \phi_{red}(\lambda) s(\lambda) \tau_0(\lambda) d\lambda$ from which the channel signals are:

$C'_{RG}(red) = L'(red) - M'(red)$ $C'_{BY}(red) = S'(red) - [L'(red) + M'(red)]$.

For the orange LED light, as colour sample 32:

$L'(orange) = \int_{380}^{780} \phi_{orange}(\lambda) l(\lambda) \tau_0(\lambda) d\lambda$ $M'(orange) = \int_{380}^{780} \phi_{orange}(\lambda) m(\lambda) \tau_0(\lambda) d\lambda$ $S'(orange) = \int_{380}^{780} \phi_{orange}(\lambda) s(\lambda) \tau_0(\lambda) d\lambda$, from which the channel signals are:

$C'_{RG}(orange) = L(orange) - M'(orange)$ $C'_{RG}(orange) = S(orange) - [L'(orange) + M'(orange)]$.

From this, the opponent channel signals are obtained in the way described above.

Following this the distance of the modified colour points R', O' is determined from each other within the coordinate system, the colour points R', O' being determined by the opponent channel signal pairs and corresponding to the colours of the red and orange LED lights. For the red-orange lights $$d_{RO} = \sqrt{[C'_{BY}(red) - C'_{BY}(orange)]^2 + [C'_{RG}(red) - C'_{RG}(orange)]^2}$$

The hue angles $\alpha'(red)$, $\alpha'(orange)$ are calculated from the modified opponent channel signal pairs using the relationship $$\alpha = arctg \frac{C'_{BY}}{C'_{RG}}$$

with respect to the colour points R', O' belonging to each colour sample 32.

Following this the differences of the hue angle sensed through the colour filter and the hue angle of the eye with normal colour vision are also determined:

$$\Delta\alpha(\text{red})=\alpha'(\text{red})-\alpha(\text{red})$$

$$\Delta\alpha(\text{orange})=\alpha'(\text{orange})-\alpha(\text{orange})$$

In the fourth step the initial function $\tau_0(\lambda)$ value is changed stepwise, using the known method of extreme-value-searching, for example, until the maximum value of $d_{RO}$ and at the same time the minimum value of the angle differences $\Delta\alpha(\text{red})$, $\Delta\alpha(\text{orange})$ are reached. A colour filter 10 with spectral transmission function $\tau(\lambda)$ corresponding to the extreme value will be the result of the present design method, which filter 10 may be manufactured using known methods in the form of work glasses, for example.

In this example it was not taken into account that the levels of brightness of the red and orange LED lights may be different. If this is to be taken into account then the brightness coordinate V belonging to the individual colour samples 32 may also be determined in a known way, for example by using a reflection spectrophotometer. In this case the above calculations are modified to the extent that the distance of the modified colour points R', O' measured from each other within a 3-dimensional coordinate system may be calculated according to the following formula:

$$d_{RO} = \sqrt{[C'_{BY}(\text{red}) - C'_{BY}(\text{orange})]^2 + [C'_{RG}(\text{red}) - C'_{RG}(\text{orange})]^2 + [C'_{RG}(\text{red}) - C'_{RG}(\text{orange})]^2}$$

In the course of the extreme value search the distance $d_{RO}$ calculated in this way is maximised, while the angle differences $\Delta\alpha(\text{red})$, $\Delta\alpha(\text{orange})$ determined above are minimised.

EXAMPLE 4

Example 4 differs from example 3 in that the colour sample set 30 consists of the basic colours of a screen of a given computer monitor type or given mobile telephone type or given tablet type or given notebook type or given television type or of a screen of other similar IT device having a screen. Generally, the screens of such IT devices produce all of the possible colours from three basic colours, and each basic colour has a specific spectrum characteristic of the device. In this case the goal is to increase colour discrimination in the interest of better colour separation, and to modify colour identification if a difference is to be provided as compared to the basic colours (for example, the goal is to display a red colour that is judged to be prettier than the red colour produced by the device).

In the case of the present example, the goal is to modify the colour vision of an eye with normal colour vision, but, naturally the colour filter 10 could also be designed for an eye with deficient colour vision.

EXAMPLE 5

In the case of this example the colour sample set 30 comprises quasi-monochromatic (in other words nearly monochromatic) colour samples 32 taken from the visible wavelength range of light every 1 to 20 nm, preferably every 5 to 15 nm, even more preferably every approximately 10 nm.

For example, colour samples are taken from the visible spectrum between 400 and 700 nm every 10 nm, thereby obtaining a colour sample set 30 of thirty colour samples 32, with respect to which the method described in the case of example 1 is carried out. The colour filter 10 obtained in this way provides satisfactory colour discrimination as well as colour identification substantially throughout the entire visible spectrum for the targeted eye 20.

EXAMPLE 6

In the case of this example the objective is to produce a colour filter set with which the colour vision of the majority of persons with deficient colour vision can be corrected. In the case of the above examples the starting point was always an eye 20 with given colour vision and its L-, M- and S-cone colour sensing receptors were characterised with the spectral sensitivity functions $l'(\lambda)$, $m'(\lambda)$ and $s'(\lambda)$. These spectral sensitivity functions may be measured for a given patient in a known way, however, the inventors have made a surprising observation: it is sufficient to determine the spectral transmission function $\tau(\lambda)$ of the desired colour filters 10 for the three spectral sensitivity functions of a small number of typical colour vision deficient receptors, with these few colour filters 10 the colour vision of the majority of persons with deficient colour vision can be satisfactorily corrected.

Approximately 23% of persons with deficient colour vision suffer from protanomaly, 73% from deuteranomaly, and approximately 4% of cases are persons with severe colour vision deficiency (protanopia and deuteranopia). The most severe colour vision deficiencies, monochromasia and total colour blindness occur only very rarely. The sensitivity of the blue-sensitive receptor, the S-cone is very rarely deficient. Faults in this receptor are usually caused by illnesses or intoxication, and when the cause is eliminated the colour vision becomes normal once again. For this reason almost 100% of persons with deficient colour vision fall into one of the protanomaly, deuteranomaly, protanopia and deuteranopia groups.

Another observation was that the spectral sensitivity function of the M-cones in practice only shifts in the direction of the spectral sensitivity function of the L-cones, and vice versa, the sensitivity function of the L-cones shifts towards the sensitivity function of the M-cones.

As a result of this a colour filter set may be designed the colour samples of which assume discrete M-cone and L-cone spectral sensitivity function displacements:

$m_1'(\lambda)=m(\lambda-x_1)$, $m_n'(\lambda)=m(\lambda-x_n)$ where $x_1 \ldots x_n$ are the numbers giving the extent of the M-cone receptor sensitivity shift expressed in nm.

$l_1'(\lambda)=l(\lambda+y_1), \ldots, l_n'(\lambda)=l(\lambda-y_n)$ where $y_1 \ldots y_n$ are the numbers giving the extent of the L-cone receptor sensitivity shift expressed in nm.

Consequently, for example, the first colour filter 10 is designed for a colour vision deficient eye 20 the sensitivity curve $m_1'(\lambda)$ of the M-cone receptor of which is shifted by x', for example by 20 nm as compared to the sensitivity curve $m(\lambda)$ of the M-cone receptor of an eye 22 with normal colour vision, in other words:

$$m_1'(\lambda)=m(\lambda-20 \text{ nm})$$

while the spectral sensitivity functions of the L-cone and S-cone colour-sensing receptors correspond to those of an eye with normal colour vision, in other words the person with deficient colour vision is suffering from deuteranomaly.

It should be noted here that the sensitivity curve of the receptors of colour deficient people is not only shifted, but also slightly distorted, hence the design procedure can be further refined if the color sensitivity curves l 'and m' are not obtained by shifting the color-sensitive sensitivity curves of people with normal colour vision but rather the colour sensitivity curves are measured for example by known microspectrophotometric methods. The curves measured in this way can still be characterized by how much the maximum of the curve is shifted relative to the maximum of the corresponding curve of a person with normal color vision.

The degree of the deuteranomaly taken into account in the case of designing the filter is given by the parameter $x_i$. Severe deuteranomaly which is close to deuteranopia is corrected by the colour filter 10 from the set of filters 10, which is designed using a spectral sensitivity function $m'(\lambda)$ of the M-cone receptors which is shifted in the longer wavelength direction to such an extent that it nearly coincides with the spectral sensitivity function $l(\lambda)$ of the L-cone receptors of an eye with normal colour vision, while the spectral sensitivity functions of the L-cone and S-cone receptors correspond to those of an eye with normal colour vision.

Similarly, the degree of the protanomaly taken into account in the case of designing the filter is given by the parameter $y_i$. Severe protanomaly which is close to protanopia is corrected by the colour filter 10 from the set of filters 10 which is designed using a spectral sensitivity function $l'(\lambda)$ of the L-cone receptors which is shifted in the shorter wavelength direction by such an extent that it nearly coincides with the spectral sensitivity function $m(\lambda)$ of the M-cone receptors of an eye with normal colour vision, while the spectral sensitivity functions of the M-cone and S-cone receptors correspond to those of an eye with normal colour vision.

According to the inventors' experience a satisfactory result may be achieved for the correction of deuteranomaly and severe deuteranomaly close to deuteranopia if the distance between the maxima of the normal sensitivity curves $m(\lambda)$ and $l(\lambda)$, which is 28 nm, is divided into two parts in such a way that $x_1$ falls between 5 and 24 nm, preferably between 10 and 20 nm, e.g. $x_1=20$ nm (moderate deuteranomaly), and $x_2$ falls between 25 and 28 nm, e.g. $x_2=26.5$ nm (severe deuteranomaly). In the case of another example one part of the 28 nm range split into two parts is divided into further two parts, therefore the entire 28 nm range is divided into a total of three parts, e.g. $x_1=15$ nm (mild deuteranomaly), $x_2=20$ nm (moderate deuteranomaly) and $x_3=25$ nm (severe deuteranomaly). In the case of another example one part of the 28 nm range split into two parts is divided into further three parts, therefore the entire 28 nm range is divided into a total of four parts, e.g. $x_1=10$ nm (mild deuteranomaly), $x_2=15$ nm (mild-moderate deuteranomaly), $x_3=20$ nm (moderate deuteranomaly) and $x_4=25$ nm (severe deuteranomaly). The inventors have found that in the case of this finer division the experience of colour vision does not improve considerably, while the designing and production of the extra colour filters requires significant investment.

The procedure is similar in the case of the correction of protanomaly and severe protanomaly close to protanopia, and a satisfactory result may be achieved in the case of most persons with deficient colour vision if the distance between the maxima of the normal sensitivity curves $m(\lambda)$ and $l(\lambda)$ is divided into two parts in such a way that $y_1$ falls between 5 and 24 nm, preferably between 10 and 20 nm, e.g. $y_1=20$ nm (moderate protanomaly), and $y_2$ falls between 25 and 28 nm, e.g. $y_2=26.5$ nm (severe protanomaly). In the case of another example one part of the 28 nm range split into two parts is divided into further two parts, therefore the entire 28 nm range is divided into a total of three parts, e.g. $y_1=15$ nm (mild protanomaly), $y_2=20$ nm (moderate protanomaly) and $y_3=25$ nm (severe protanomaly). In the case of another example one part of the 28 nm range split into two parts is divided into further three parts, therefore the entire 28 nm range is divided into a total of four parts, e.g. $y_1=10$ nm (very mild protanomaly), $y_2=15$ nm (mild protanomaly), $y_3=20$ nm (moderate protanomaly) and $y_4=25$ nm (severe protanomaly). It was found that in the case of this finer division the experience of colour vision does not improve considerably, while the designing and production of the extra colour filters requires significant investment.

During the filter design method, preferably similarly to example 5, colour samples are taken from the visible light spectrum frequently, e.g. every 1 to 10 nm, and the extreme value search is performed for the colour sample set 30 obtained in this way.

In the case of two types of M-cone receptor model and two types of L-cone model the set will contain a total of four types of colour filter 10, and surprisingly even with this set the colour vision of the majority of persons with deficient colour vision may be corrected with a good result both in terms of colour discrimination and colour identification.

In the case of three types of M-cone receptor model and three types of L-cone model a total of six types of colour filter 10 may be designed, with which the colour vision of the majority of persons with deficient colour vision may be corrected with an even better result both in terms of colour discrimination and colour identification.

It was found that correction providing an almost perfect colour vision experience may be achieved for the large majority of persons with deficient colour vision (approx. 95%) in the case of just four types of M-cone model and four types of L-cone model, which means there are a total of eight types of colour filter in the colour filter set.

The advantage of the pre-designed colour filter set is that the spectral sensitivity functions $l'(\lambda)$, $m'(\lambda)$ and $s'(\lambda)$ of the L-, M- and S-cone receptors do not have to be separately recorded for each and every patient with deficient colour vision, and the colour filter 10 required for performing the correction does not have to be designed for each person and manufactured according to unique parameters, instead the pre-manufactured colour filter corresponding the closest to the diagnosis is used. In the case of a relatively small number of well-designed colour filters the colour filter 10 that is the most appropriate for the given person may be easily and quickly selected.

EXAMPLES

In the following a specific design process is disclosed for designing four types of color filters to improve color vision, namely:

a color filter to correct mild to moderate deuteranomaly,
a color filter to correct severe deuteranomaly,
a color filter to correct mild to moderate protanomaly, and
a color filter to correct severe protanomaly.

We speak of severe deuteranomaly when the maximum of the deuteros sensitivity curve is shifted to the right by approx. 25 nm or more (i.e., toward high wavelengths). Below this value, we speak of mild to moderate deuteranomaly, depending on the degree of shift.

Similarly, we speak of severe protanomaly when the maximum of the protos sensitivity curve is shifted to the left by approx. 25 nm or more (i.e., in the direction of the small wavelength). Below this value, we speak of mild to moderateprotanomaly, depending on the degree of displacement.

Mild to Moderate Deuteranomaly

When designing the color filter to correct mild to moderate deuteranomaly, we started out from the measured deuteros sensitivity curve of a person with deutan colour vision deficiency having a deuteros sensitivity curve the maximum of which was shifted by approx. 18 nm to the right relative to the normal deuteros sensitivity curve, while the tritos and protos sensitivity curves were the same as the corresponding sensitivity curves for normal colour vision (the values of which were considered according to the technical literature). As conventional, the sensitivity curves relate to an eye adapted to a color temperature of 5500 K and a viewing angle of 10°. It is noted here that in the case of an eye having normal color vision which is adapted to higher or lower color temperatures, the location of the maximum of the sensitivity curve of each receptor and the distances therebetween change slightly, whereby the spectral transmission profile of the color filter designed by the method according to the invention depends somewhat on the colour temperature to which the normal eye is adapted to. This also means that during the design it is possible to determine under which ambient lighting conditions the color filter will work optimally.

In order to ensure, as far as possible, correct color perception within the entire visible spectrum, a set of color samples consisting of color samples taken every 5 nm from the wavelength range of visible light was chosen. As the starting filter, a filter with a spectral transmission function $\tau_0(\lambda)$ of constant value 1 was chosen, i.e. a perfectly permeable filter.

Subsequently, with the deuteros sensitivity curve shifted by 18 nm and the tritos and protos sensitivity curves corresponding to the normal colour vision vision, for all the color samples the receptor signals of the colour deficient person were determined according to the formulas presented above and the red-green and blue-yellow opponent channel signals were determined therefrom using the current (or initial) filter characteristic. From the channel signals the color point coordinates for the examined color samples were obtained.

The above operations were also performed with the three sensitivity curves of normal colour vision.

After this, the extreme value search algorithm was selected, which was a known genetic algorithm in the present example. To apply the genetic algorithm, the fitness value conditions were specified, in this case the distance between the color point coordinates interpreted in the coordinate system corresponding to the channels of the channel signals (discrimination criterion), and the angular differences from the corresponding reference color points (identification criterion) and their weighting. Appropriate weight factors can be used, for example, to ensure that the discrimination between certain color samples is more important, or e.g. the ability to better identify certain colour samples. In a preferred embodiment, the weighting was used to take greater account of the discrimination of the green and orange color samples relative to each other. The latter is only averagely important for ensuring a good color vision experience; however, for the so-called Ishihara test which is a commonly used colour vision diagnosis, the distinction between green and orange plays a prominent role. Better performance of any other condition can be ensured as well by applying appropriate weight factors. In addition, any additional design parameter may be considered with an additional fitness value condition, such as the requirement that the total transmission of the filter be as large as possible within the visible light range. The importance of this criterion in relation to the discrimination and identification requirements can also be adjusted by applying weight factors.

After setting the fitness value, the genetic algorithm was run iteratively on the current input data to improve the fitness value associated with the current filter.

Specific ranges of the filter characteristic were set as the variables of the genetic algorithm (e.g. the 34th algorithm variable=the average transmission between 530-535 nm). The number of algorithm variables correspond to the number of ranges selected within the visible range.

In each iteration, the genetic algorithm calculated the actual fitness value for the given input data (model of colour vision deficiency, colour sample, current filter characteristic).

The genetic algorithm tested algorithm-variable combinations in each iteration that performed better based on the fitness value compared to previous iterations. Because combining "more successful" filter characteristics with each other usually leads to a better fitness value, with iteration, the filter characteristic leads to an optimum that meets the fitness value criteria.

The genetic algorithm was run on the filter transmission curve up to a predefined threshold or time. When the acceptable limit was reached, the iteration was stopped and the resulting filter transmission curve was accepted as the quasi-best correction corresponding to the input values.

Figure 10:
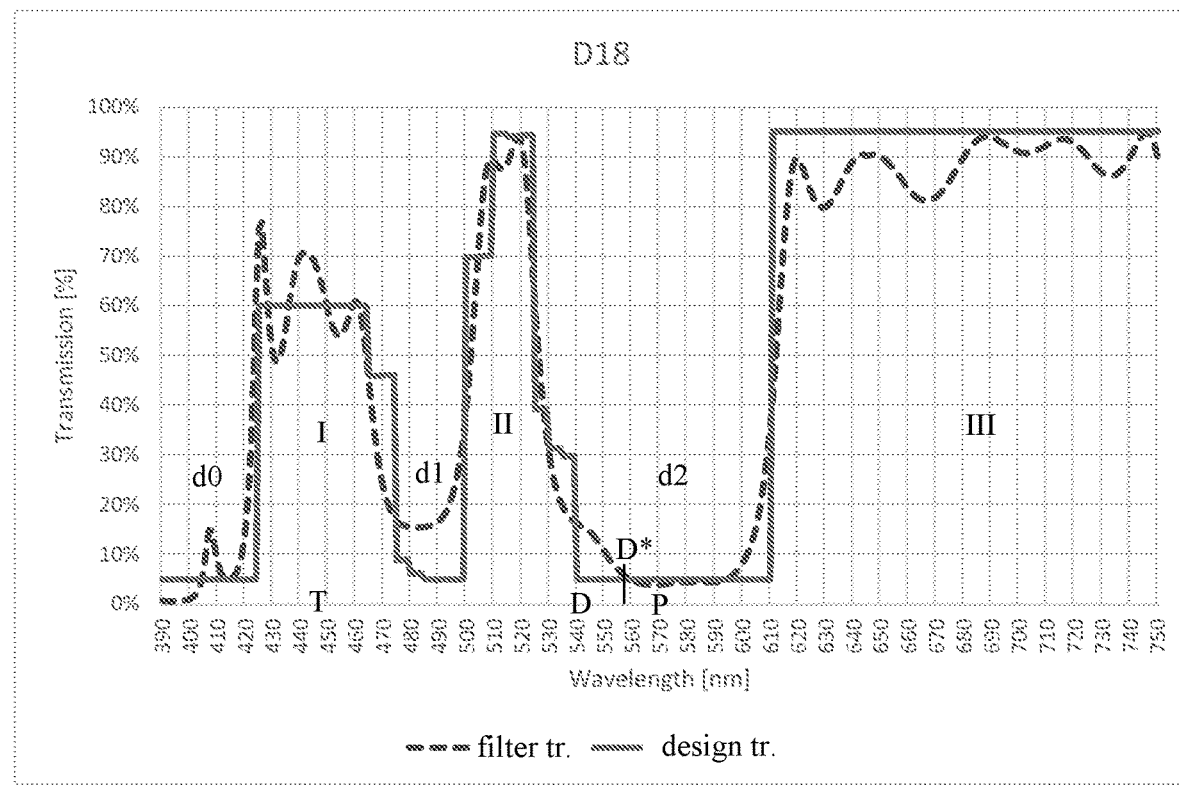
FIG. 10 is a graph showing a design transmission curve obtained by an exemplary filter design method and a transmission curve of a filter manufactured therefrom.

For the sake of manufacturability, the narrow, spike-like jumps were cut off on the resulting transmission curve, resulting in a stepwise design transmission curve indicated with a solid line in FIG. 10.

The design transmission curve was used as a starting point to design a colour filter based on thin film technology. A number of known design algorithms are available to design the thin film structure. The dashed line curve in FIG. 10 is a transmission function of a colour filter produced by an optical thin film design software called FilmStar, which clearly follows the characteristics of the design transmission curve. In the case of thin-layer design, we limited the number of thin layers in 40 layers, however, by allowing more layers the design curve which is considered optimal can be followed even more accurately. Technology other than thin film technology can be used to create the desired transmission profile, such as dyeing and colouring methods well known to those skilled in the art.

The design procedure was repeated for several subjects with mild to moderate deuteranomaly for whom the maximum of the measured deuteros sensitivity function was shifted by approx. 15 to 20 nm with respect to normal vision. Similar filter characteristics were obtained in the repeated design procedures. By testing the efficiency of the obtained filters, we found that in the case of deuteranomaly which is not severe, colour vision can be well corrected with a colour filter the spectral transmission function of which shows the following characteristics:

It contains a first deutan passband that has a full-width at half maximum (FWHM) of approx. 30 to 60 nm, an approximately flat top and a centre wavelength between approx. 420 to 460 nm. In the denomination of the first deutan passband, the word "deutan" appears solely for the purpose of making it easier to distinguish it from the passbands of the colour filters for correcting protanomaly which are to be presented later. Hereinafter, the adjective "deutan" will be used in a similar way to other elements of the transmission function. The lower and upper limiting wavelengths, which determine the FWHM are, as conventional, the two wavelengths at which the value of the transmission is half of the maximum value within the passband. The FWHM is thus the difference between the upper and lower limiting wavelengths. The centre wavelength is the lower limiting wavelength plus half the FWHM. In the context of the present invention, the passband is considered to be located between the two limiting wavelengths, i.e. the boundaries of the passband are located at the wavelengths where the transmission is halved relative to the maximum within the band. The average transmission within the first deutan passband defined by the FWHM is preferably between 50 and 80%. In FIG. 10, which is an exemplary filter, d-I indicates the portion corresponding to the first deutan passband. Note that the transmission design curve shown with solid line in FIG. 10 and the band boundaries of the dashed line curve obtained by thin film technology (not marked separately) do not match because the manufacturing technology does not allow accurate tracing of the design curve, however, it appears that both the design curve and the filter curve fall within the specified preferred parameter ranges. For the passbands discussed below, what is stated herein is applicable mutatis mutandis.

The spectral transmission function contains a second deutan passband that has an FWHM of approx. 20 to 80 nm and a centre wavelength between approx. 500 and 530 nm. The transmission at the peak of the second deutan passband is preferably at least 70%. In FIG. 10, the part corresponding to the second deutan passband is denoted by II.

The spectral transmission function further comprises a third deutan passband having an FWHM of at least approx. 120 nm, an approximately flat top, and the lower limit of the band is between approx. 590 and 620 nm. In the embodiment shown in FIG. 10, the third deutan passband transmits light over the entire visible range above its lower boundary limit (i.e. towards the higher wavelengths); at higher frequencies (above about 750 nm) the transmission profile of the filter no longer affects color vision, therefore the upper band limit is considered to be 750 nm. The average transmission of the third deutan passband (in the visible range up to 750 nm) is preferably at least 80%. In FIG. 10, the portion corresponding to the third deutan passband is indicated by III.

Between the first and second deutan passbands there is a first deutan stopband with an average transmission of at least approx. less than 25%, preferably less than 20%, more preferably less than 10% over a wavelength range of at least about 20 nm. Since the passbands are limited by the lower and upper limiting wavelengths defining the FWHM, it is practical to consider that the adjacent stopband starts from here. For this reason, on the one hand, the value of the transmission may differ significantly at the two boundaries of the stopband, and on the other hand, the transmission may be relatively high at these boundaries. For this reason, it is more useful to characterize the stopband by the width of its strongest blocking range and the transmission here. Note that the passband surrounded by two stopbands always "stands out" from the adjacent stopbands, which can be quantified by that the transmission maximum of the passband is at least twice the transmission minimum of the adjacent stopband. The first deutan stopband is denoted by d1 in FIG. 10.

A second deutan stopband is formed between the second and third deutan passbands, the average transmission of which over at least 20 nm is less than 25%, preferably less than 20%, more preferably less than 10%. The second deutan stopband is denoted by d2 in FIG. 10.

Preferably, the first deutan passband is bounded from the left (i.e. from the direction of the smaller wavelengths) by a steep cut-off and a subsequent stopband, the average transmission of which is preferably less than 15%, more preferably less than 10%. In FIG. 10, this stopband is denoted by d0.

Accordingly, this is a so-called multi-bandpass filter, i.e. a filter with multiple passbands. The filters to be presented later are also multi-bandpass filters.

Figure 1:
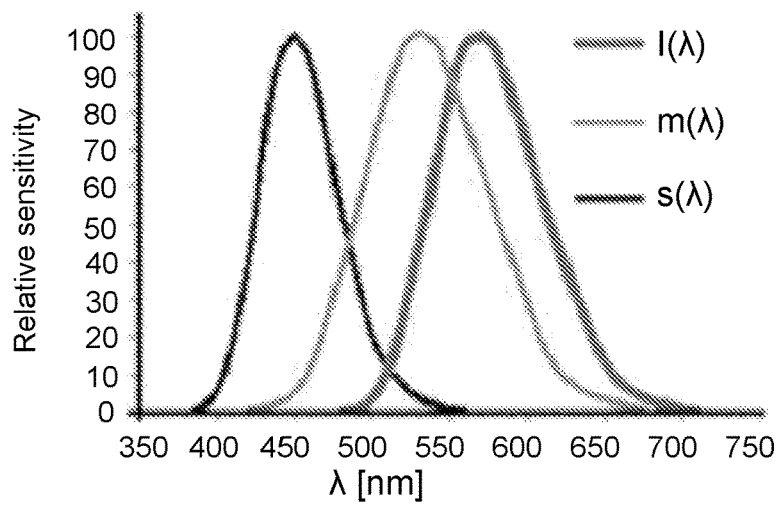
Figure 3:
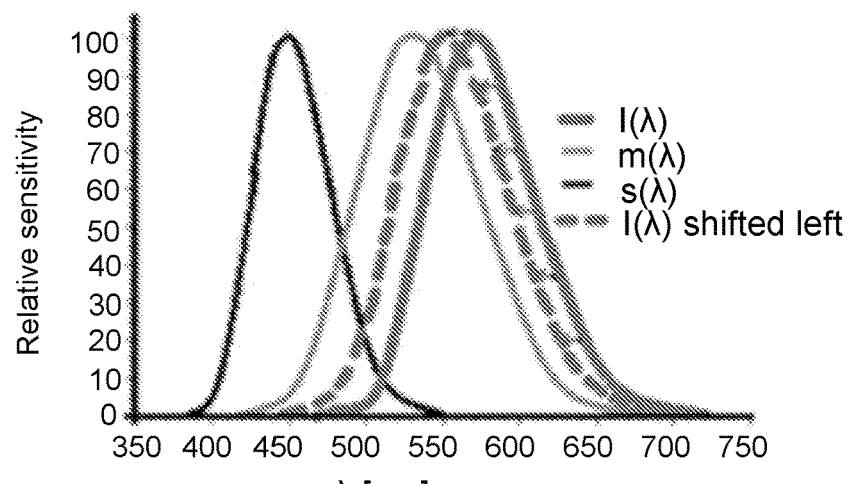
FIG. 3 depicts the shift in spectral sensitivity of protanomaly.
Figure 4:
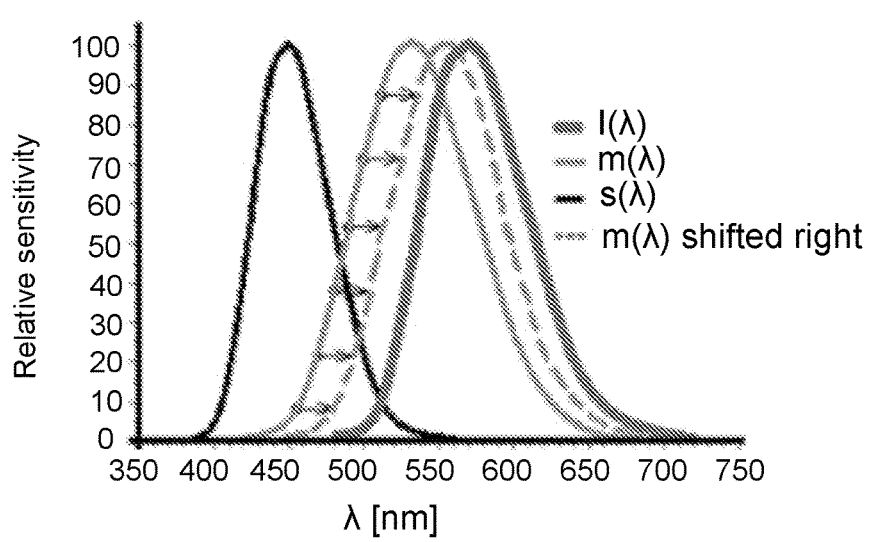
FIG. 4 depicts the shift in spectral sensitivity of deuteranomaly.
Figure 2A:
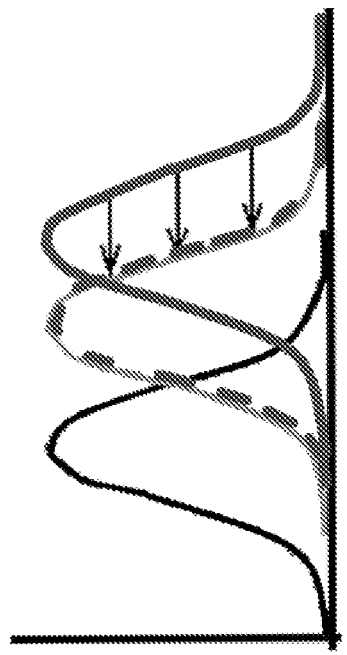
Figure 2B:
Figure 2C:
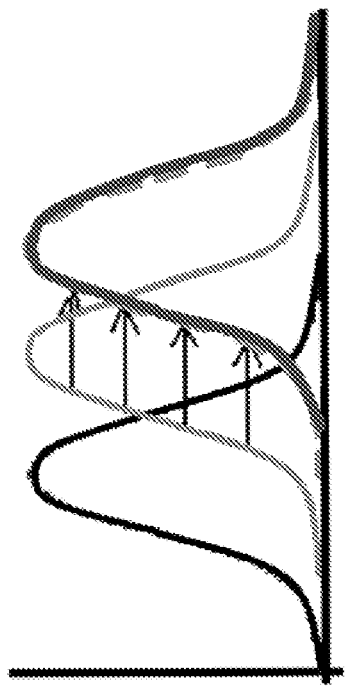
Figure 2D:
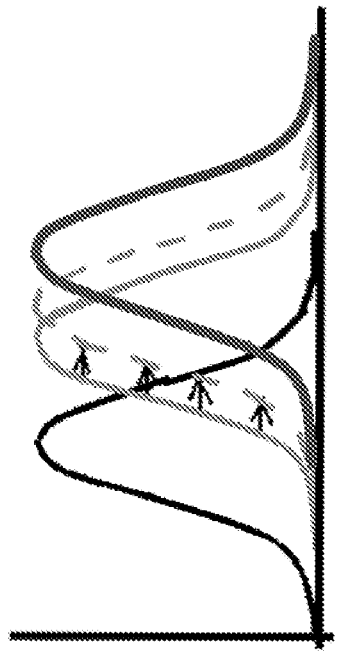
Figure 5:
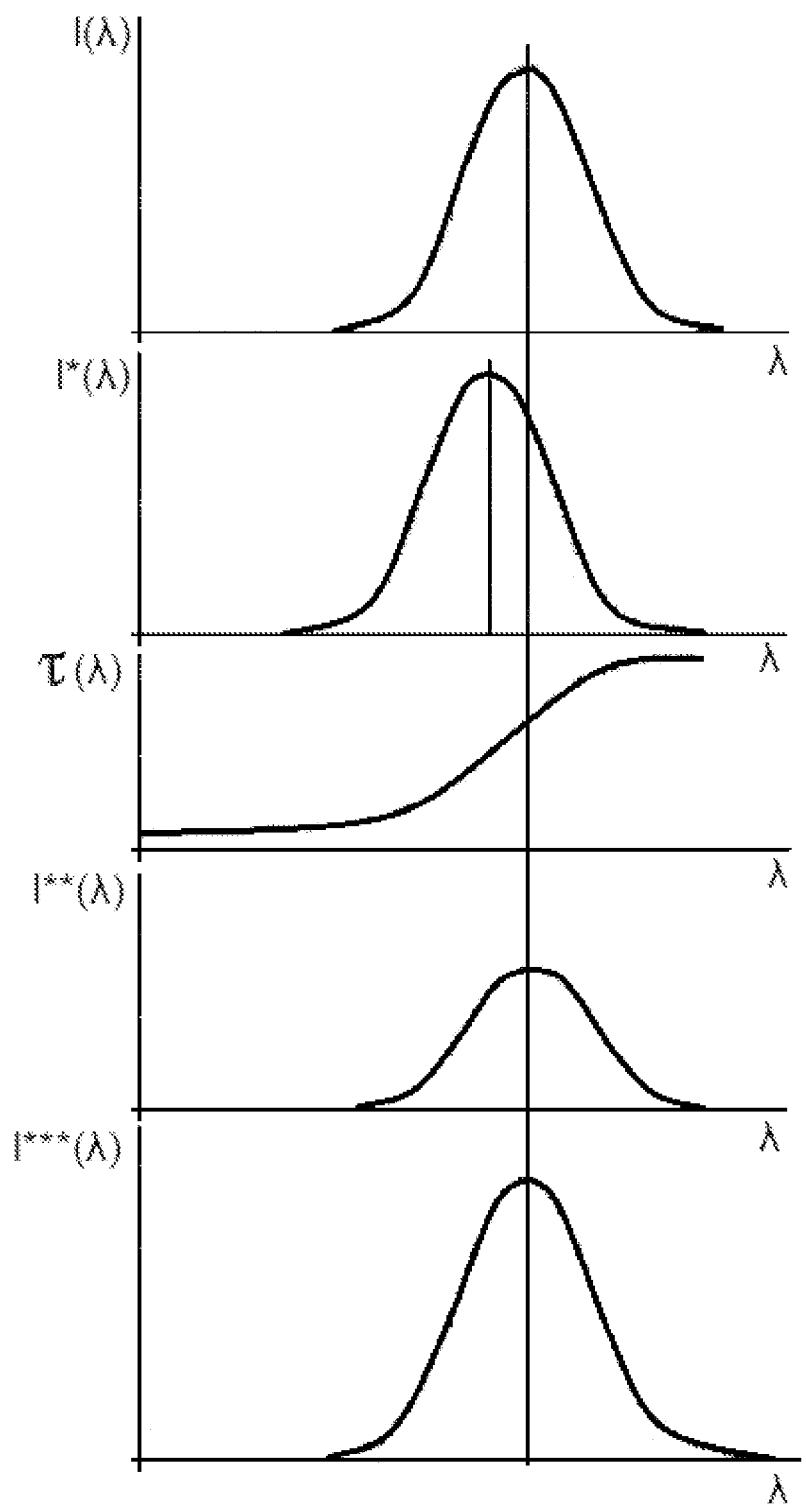
FIG. 5 depicts a series of graphs illustrating the traditional correction of colour vision deficiency.

The inventors have found that the above-listed characteristics of the optimal colour filter for correcting mild to moderate deuteranomaly obtained by the design method of the present invention have the following physical-biological effects. In the case of deuteranomaly, of the sensitivity functions shown in FIG. 1, the maximum of the sensitivity function of the deuteros receptor that is normally at approx. 540 nm is shifted to the right, as illustrated in FIG. 2c. Because of this, the deuteros and protos sensitivity curves overlap more than normal, so the discrimination and identification of green, yellow, orange, and red also deteriorates. The maximum location of the deuteros sensitivity curve of the normal colour vision is indicated with D, while the maximum location of the colour deficient deuteros sensitivity curve which is shifted by 15 nm in the example above is indicated with D*, the maximum location of the protos sensitivity curve (for both normal colour vision and deuteranomal colour deficiency) is indicated with P, the maximum location of the tritos sensitivity curve (for both normal colour vision and deuteranomal colour deficiency) is indicated by T on the wavelength axis. It is clear from the stepwise design transmission profile (solid line) that in order to correct colour vision the transmission in the overlapping wavelength range is greatly reduced by the second stopband d2, which is advantageous for reducing over-sensitivity due to aggregation. The deuteros receptor is allowed to function within the second deutan passband II. The first stopband d1 limits the corrected deuteros curve from the direction of the smaller wavelengths, which, through the adaptation mechanism described in connection with FIG. 5, helps to amplify the sensitivity of the deuteros receptor within the wavelength range where transmission is allowed by the second passband II. However, the first stopband d1 also takes away from the detection region of the tritos receptor, so it is advantageous to delimit it from the left with the stopband d0 in order to improve the sensitivity within the remaining wavelength range so that the sensitivity of the tritos does not shift to the left. For the protos receptor, in this embodiment a high transmission from 610 nm upwards is provided by the third passband III, so as not to limit the protos sensitivity curve. The left rising edge of the third passband III is preferably nearly vertical, the average slope being at least such that the transmission increases by at least 30% over 10 nm, preferably by at least 40% over 10 nm, so that the sensitivity of the protos receptor which is blocked in the overlapping wavelength range by the second stopband d2 increases in the direction of the higher wavelengths as early as possible.

At the same time, these measures improve the ability of the colour deficient person having deuteranomaly to discriminate and identify colours (primarily green and red, and the colours in between). It is noted here that although transmission is strongly blocked over the wavelength range corresponding to yellow, the inventors have recognized that this does not result in stopping the colour deficient person from seeing the colour yellow. This is because naturally occurring colours are not monochromatic, instead a broadband spectrum makes up the perceived colour, so there is always enough information left in the unfiltered part of the spectrum to sense the given colour.

Severe Deuteranomaly

When designing the color filter to correct severe deuteranomaly, the above described design method was carried out analogously. We started out from the measured deuteros sensitivity curve of a person with deutan colour vision deficiency having a deuteros sensitivity curve the maximum of which was shifted by approx. 25 nm to the right relative to the normal deuteros sensitivity curve, while the tritos and protos sensitivity curves were the same as the corresponding sensitivity curves for normal colour vision.

Figure 11:
FIG. 11 is a graph showing a design transmission curve obtained by another exemplary filter design method and a transmission curve of a filter made therefrom.

For the sake of manufacturability, the narrow, spike-like jumps were cut off on the resulting transmission curve, resulting in a stepwise design transmission curve indicated with a solid line in FIG. 11.

The design transmission curve was used as a starting point to design a colour filter based on thin film technology. The dashed line curve in FIG. 11 is a transmission curve of a colour filter produced by the optical thin film design software called Film Star, which clearly follows the characteristics of the design transmission curve. In the case of thin-layer design, we limited the number of thin layers in 40 layers. Technology other than thin film technology can be used to create the desired transmission profile, such as known dyeing and colouring methods.

The design procedure was repeated for several subjects with severe deuteranomaly for whom the maximum of the measured deuteros sensitivity function was shifted by approx. 24 to 26 nm with respect to normal vision. Similar filter characteristics were obtained in the repeated design procedures. By testing the efficiency of the obtained filters, we found that in the case of severe deuteranomaly, colour vision can be well corrected with a colour filter the spectral transmission function of which shows the following characteristics:

It contains a fourth deutan passband with a peak (transmission maximum) is between approx. 410 and 425 nm. The use of the term "fourth" merely serves to distinguish it from the adjectives "first", "second" and "third" used in connection with the previously described filter and does not mean that in the present case another three passbands would precede the fourth passband. At the peak of the fourth deutan passband, the transmission value is preferably between approx. 50 and 90%, more preferably at least 60%. The peak of the fourth deutan passband is narrow, preferably having an FWHM of at least 10 nm. Preferably, to the left of the peak within approx. 10 to 20 nm, the transmission drops by approx. half of the transmission measured at the peak, and preferably stays at approx. this value until the lower wavelength limit of visible light. In FIG. 11, which shows an exemplary filter, the part of the transmission curve corresponding to the fourth deutan passband is indicated with IV.

The filter transmission function designed to correct severe deuteranomaly contains a fifth deutan passband with an FWHM of 20 to 60 nm and a centre wavelength between 460 to 490 nm. The transmission of the peak of the fourth deutan passband is preferably at least 70%. In FIG. 11, the part corresponding to the fifth deutan passband is denoted by V.

The transmission function also includes a sixth deutan passband with an FWHM of at least 120 nm, which has an approximately flat top, and a lower limit of the FWHM is between 590 and 610 nm. Similarly to the mild-to-medium correction filter, the embodiment shown in FIG. 11 has a high transmission to the right of the lower band boundary of the sixth deutan passband over the entire visible range, preferably with an average transmission of at least 80% (taking the passband into consideration only until 750 nm as upper limit). In FIG. 10, the part corresponding to the sixth deutan passband is denoted by VI.

Between the fourth and fifth deutan passbands there is a third deutan stopband with an average transmission of less than 25% over a wavelength range of at least 20 nm. In the embodiment shown in FIG. 11, this stopband is denoted by d3.

Between the fifth and sixth deutan passbands, a fourth deutan stopband is formed, the average transmission of which over a wavelength range of at least 30 nm is less than 20%, preferably less than 10%. This is denoted by d4 in FIG. 11.

The transmission of the peak of the fourth deutan passband is preferably at least 60%, the transmission of the peak of the fifth deutan passband is preferably at least 70%, and the average transmission within the FWHM of the sixth deutan passband is preferably at least 80%.

In the case of the filter correcting severe deuteranomaly, the inventors have also recognized the physical-biological effects of the above features, which improve the ability of a person with severe deuteranomaly to distinguish between green and red colours and the colours between them (colour discrimination) and to recognize these colours (colour identification). Only the differences compared to the previously described embodiment will be discussed herein. Since in the case of severe deuteranomaly (close to deuteranopia) the location of the maximum of the deuteros sensitivity curve (D*) is shifted by even more in the direction of the location of the maximum of the protos sensitivity curve (P), the two almost coincide, hence the effects described earlier are needed in a more intense form. Accordingly, the peak of the fifth passband V, which serves to shift the deuteros sensitivity curve, is further to the left, and the fifth passband V is limited from the left by the third stopband d3 to increase the otherwise significantly limited deuteros sensitivity curve. However, the third stopband d3 also takes away from the sensitivity range of the tritos receptor, hence, a relatively larger transmission must be provided to the left of the third stopband d3 within the fourth passband IV. Again, the protos receptor sensitivity curve is allowed to operate in the higher wavelength range by the sixth passband VI functioning as a high-transmission, high-pass filter. As the protos receptor works well, the sixth passband VI is bounded by a steep (almost vertical) rising edge from the left, the average slope of which in this case is at least such that the transmission increases by at least 30%, preferably by at least 40% over 10 nm.

These measures improve, at the same time, the ability to distinguish and identify colours (primarily green and red, and the colours in between) for a person with severe deuteranomaly (close to deuteranopia).

Mild to Moderate Protanomaly

When designing the color filter to correct mild to moderate protanomaly (hereinafter simply protanomaly), the above described design method was carried out analogously.

We started out from the measured protos sensitivity curve of a person with protan colour vision deficiency having a protos sensitivity curve the maximum of which was shifted by approx. 18 nm to the left relative to the normal protos sensitivity curve, while the tritos and deuteros sensitivity curves were the same as the corresponding sensitivity curves for normal colour vision.

Figure 12:
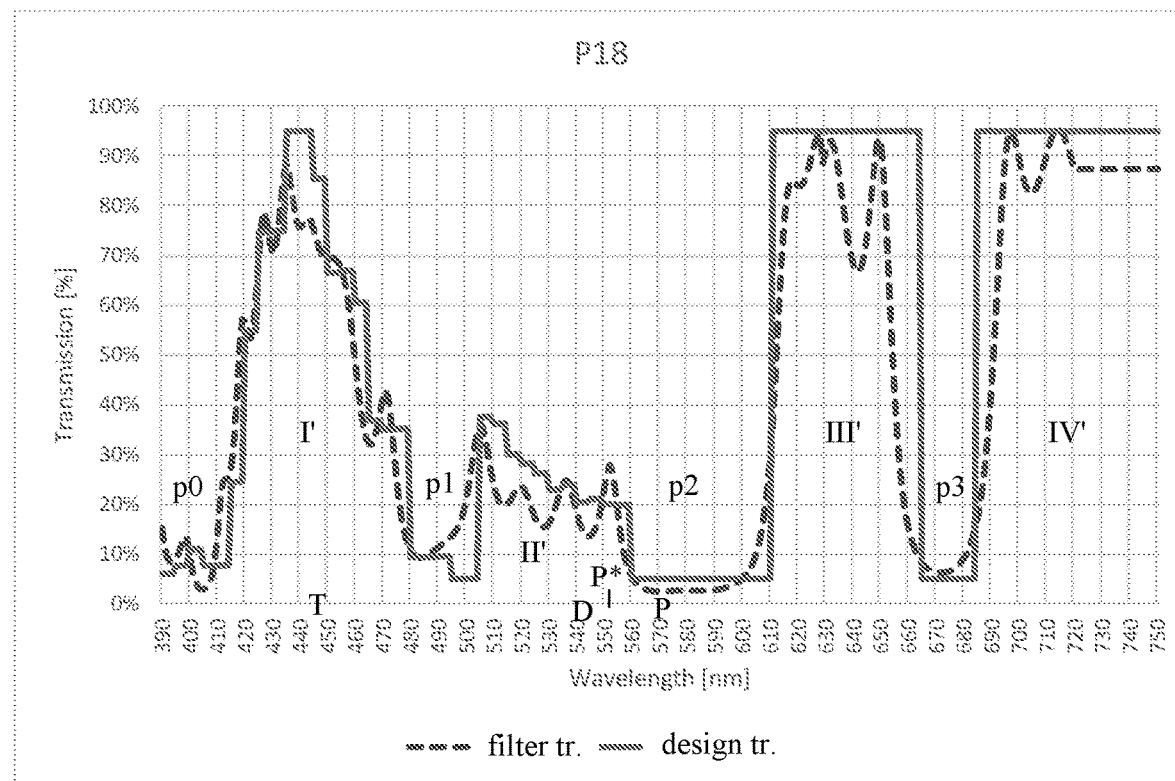
FIG. 12 is a graph showing a design transmission curve obtained by a further exemplary filter design method and a transmission curve of a filter manufactured therefrom.

For the sake of manufacturability, the narrow, spike-like jumps were cut off on the resulting transmission curve, resulting in a stepwise design transmission curve indicated with a solid line in FIG. 12.

The design transmission curve was used as a starting point to design a colour filter based on thin film technology. The dashed line curve in FIG. 12 is a transmission curve of a colour filter produced by the optical thin film design software called FilmStar, which clearly follows the characteristics of the design transmission curve. In the case of thin-layer design, we limited the number of thin layers in 40 layers. Technology other than thin film technology can be used to create the desired transmission profile, such as known dyeing and colouring methods.

The location of the maximum of the protos sensitivity curve shifted to the left by 18 nm is indicated by P* in FIG. 12.

The design procedure was repeated for several subjects with mild to moderate protanomaly for whom the maximum of the measured protos sensitivity function was shifted by approx. 15 to 20 nm with respect to normal vision. Similar filter characteristics were obtained in the repeated design procedures. By testing the efficiency of the obtained filters, we found that in the case of protanomaly, colour vision can be well corrected with a colour filter the spectral transmission function of which shows the following characteristics:

It has a first protan passband with an FWHM of 30 to 60 nm and a centre wavelength between 425 and 455 nm. In the denomation of the first protan passband, the word "protan" appears solely for the purpose of making it easier to distinguish it from the passbands of the colour filters for the correction of deuteranomaly. Hereinafter, the adjective "protan" is used in a similar way for other elements of the transmission function. The transmission of the peak (i.e., the transmission maximum) of the first protan passband is preferably at least about 60%. In FIG. 12, which shows an exemplary filter, I' denotes the portion corresponding to the first protan passband.

The spectral transmission function contains a second protan passband having an inclined top the transmission of which increases in the direction of smaller wavelengths, It has an FWHM of approx. 40 to 60 nm and it is located so that the lower band boundary is between 495 and 515 nm. The transmission of the peak of the second protan passband, which is on the left side of the band, is preferably 25-60%. In FIG. 12, the portion corresponding to the second protan passband is denoted by II'.

The spectral transmission function further comprises a third protan passband having a lower band boundary between 590 and 620 nm and an upper boundary between 645 and 670 nm, and an average transmission of the third protan passband is at least 80%. In FIG. 12, the portion corresponding to the third protan passband is indicated by III'.

A first protan stopband is formed between the first and second protan passbands, the average transmission of which is less than 20% over a range of at least 20 nm. The first protan stopband is indicated by p1 in FIG. 12.

Between the second and third protan passbands there is a second protan stopband with an average transmission that is less than 20%, preferably less than 10% over a range of at least 20. The second protan stopband is indicated by p2 in FIG. 12.

The filter for correcting protanomaly preferably also comprises a fourth protan passband, which preferably has an approximately flat top and which is located along the spectrum such that the lower limit of the band is at a distance of 20 to 40 nm from the upper limit of the third protan passband III'. In FIG. 12, the portion corresponding to the fourth protan passband is denoted by IV'. In this embodiment, the fourth protan passband IV' transmits light to the right of the lower band boundary (i.e., toward the higher wavelength) over the entire visible range, at higher frequencies (above about 750 nm) the transmission profile of the filter no longer affects colour vision. The average transmission of the fourth protan passband is preferably at least 80% in the visible range up to 750 nm.

A third protan stopband is formed between the third and fourth protan pass bands III', IV', the average transmission of which is less than 25%, preferably less than 20% over a range of at least 10 nm. The third protan stopband is indicated by p3 in FIG. 12.

Preferably, the first protan passband is also bounded from the left (i.e. from the direction of the smaller wavelengths) by a steep cut-off and a subsequent stopband, the average transmission of which is preferably less than 15%, more preferably less than 10%. In FIG. 12, this blocking band is denoted by p0 and has the same function as the blocking band denoted by d0.

The inventors have found that the physical-biological effects of the above-mentioned characteristics of the optimal colour filter for correcting mild to moderate protanomaly obtained by the design method according to the invention are as follows. In the case of protanomaly, of the sensitivity functions shown in FIG. 1, the maximum of the sensitivity function of the protos receptor, which is normally at about 568 nm, is shifted to the left, as illustrated in FIG. 2a. Because of this, the deuteros and protos sensitivity curves overlap more than normal, so the discrimination and identification of green, yellow, orange, and red deteriorates. The location of the maximum of the protos sensitivity curve of normal colour vision is indicated by P, the location of the maximum of the colour vision deficient person, which is shifted by 18 nm in the example above, is indicated by P*, the maximum location of the deuteros sensitivity curve (for both normal colour vision and protanomal colour deficiency) is indicated with D, the maximum location of the tritos sensitivity curve (for both normal colour vision and deuteranomal colour deficiency) is indicated by T on the wavelength axis. It is clear from the stepwise design transmission profile (solid line) that in order to correct colour vision the transmission in the overlapping wavelength range is greatly reduced by the second protan stopband p2, the transmission curve starts to rise again in the direction of smaller wavelengths. With this transmission profile, the deuteros sensitivity function is artificially shifted to the left, similar to the filter correcting deuteranomaly. However, since in the present case the deuteros sensitivity curve of the colour deficient subject was originally in the correct position and the tritos sensitivity curve is on the left, the relative transmission is also reduced in addition to the shifting, which is achieved by allowing significantly lower transmission in the second passband II' provided for influencing the functioning of the deuteros receptor than in the first I' and third III' passbands serving to affect the function of the tritos and protos receptors. The first stopband p1 limits the artificially shifted deuteros curve from the left, which in this case helps to prevent the deuteros receptor's sensing region from slipping abnormally onto the tritos receptor's sensing region, since if almost the same transmission would be allowed here as within the second passband II', then the sensitivity of the deuteros receptor, having been forced out of its original range, would increase within the range of the first stopband p1 as well due to the adaptation mechanism described in connection with FIG. 5. However, the first stopband p1 also takes away from the detection region of the tritos receptor, so it is advantageous to delimit the first passband I' from the left in order to increase the tritos sensitivity within the first passband I'. The peak of the first passband I' is preferably in the vicinity of the maximum location T of the tritos sensitivity curve, and the transmission is high, preferably approx. as large as in the third passband III'.

The protos sensitivity, which is shifted to the left is removed by the second stopband p2 from the wavelength range of the abnormal overlap of the deuteros and protos sensitivity curves that provides a faulty receptor signal. In the case of the present embodiment as well, a high transmission of about 80% is provided for the protos receptor above about 610 nm, in order to allow the sensitivity curve of the faulty protos to move toward higher wavelengths. The left rising edge of the third passband III' is preferably nearly vertical, the average slope being at least such that the transmission increases by at least 30%, preferably by at least 40% over 10 nm.

Since the protos sensitivity curve is shifted to the left, only the decreasing portion of the shifted sensitivity curve falls in the third passband III'. In order to increase the sensitivity here, however, it is useful to greatly reduce the transmission at the right edge of the curve by using the third stopband p3. If thin-film technology is used for production, starting from a substrate having almost 100% transmission in the visible light range, it is preferred to allow high transmission again after the third stopband p3, as this is easier to implement from the point of view of the manufacturing technology. Accordingly, on the right side of the third stopband p3, it is preferred to provide the fourth passband, denoted by IV' in FIG. 12.

These measures improve, at the same time, the ability to distinguish and identify colours (primarily green and red, and the colours in between) for a person with protanomaly.

Severe Protanomaly

When designing the color filter to correct severe protanomaly, the above described design method was carried out analogously. We started out from the measured protos sensitivity curve of a person with protan colour vision deficiency having a protos sensitivity curve the maximum of which was shifted by approx. 25 nm to the left relative to the normal protos sensitivity curve, while the tritos and deuteros sensitivity curves were the same as the corresponding sensitivity curves for normal colour vision.

Figure 13:
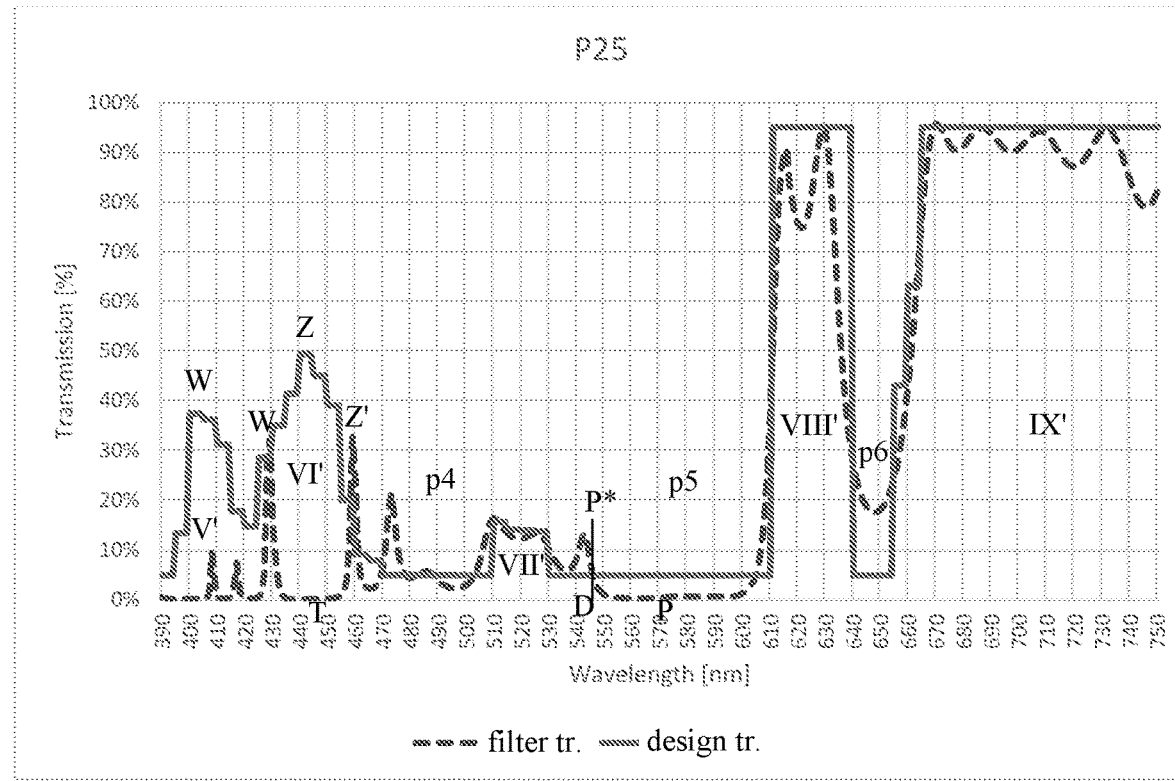
FIG. 13 is a graph showing a design transmission curve obtained by a further exemplary filter design method and a transmission curve of a filter made therefrom.

For the sake of manufacturability, the narrow, spike-like jumps were cut off on the resulting transmission curve, resulting in a stepwise design transmission curve indicated with a solid line in FIG. 13.

The design transmission curve was used as a starting point to design a colour filter based on thin film technology. The dashed line curve in FIG. 13 is a transmission curve of a colour filter produced by the optical thin film design software called FilmStar, which clearly follows the characteristics of the design transmission curve. In the case of thin-layer design, we limited the number of thin layers in 40 layers. Technology other than thin film technology can be used to create the desired transmission profile, such as known dyeing and colouring methods.

The design procedure was repeated for several subjects with severe protanomaly for whom the maximum of the measured protos sensitivity function was shifted by approx. 24 to 26 nm with respect to normal vision. Similar filter characteristics were obtained in the repeated design procedures. By testing the efficiency of the obtained filters, we found that in the case of severe protanomaly, colour vision can be well corrected with a colour filter the spectral transmission function of which shows the following characteristics:

It contains between 395 and 470 nm, fifth and sixth protan passbands with an average transmission of more than 20%, preferably between 30 and 60%. The terms "fifth" and "sixth" are used merely to distinguish these passbands from the first, second, third, and fourth passbands used previously in connection with the filter for correcting protanomaly, which does not mean that in the present case another four passbands precede the fifth. In FIG. 13, the fifth and sixth protan passbands are denoted by V' and VI', and their transmission peaks are denoted by the letters W and Z in the design transmission curve. In the transmission curve of the resulting thin-film filter, the corresponding peaks are denoted by the letters W' and Z". It can be observed that in the design transmission curve the peaks W, Z belong to the fifth and sixth passbands V', VI' having an FWHM of approx. 15 nm and 30 nm, while the peaks W', Z" of the filter obtained by the thin-film design process are more significant transmission spikes that stand out from their environment and which are quite narrow, having an FWHM of less than 0.5. This is because we started out from a carrier with nearly 100% transmission in the visible range and limited the number of thin films to 40. By allowing a larger number of thin films or by using other manufacturing technology, the design transmission profile considered optimal can be more accurately traced.

The transmission function of the filter for correcting severe protanomaly includes a seventh protan passband with an FWHM of 20 to 40 nm, a lower band boundary of which is between 500 and 515 nm and has an inclined top with an increasing transmission in the direction of the low wavelengths and has an average transmission of less than 20%, preferably approx. 10-20%. In FIG. 13, the portion corresponding to the seventh protan passband is denoted by VII'.

The transmission function also includes an eighth protan passband with an FWHM of 20 to 40 nm, a lower band boundary between 590 and 615 nm, and an average transmission of at least 80%. In FIG. 13, the portion corresponding to the eighth protan passband is denoted by VIII'.

The seventh protan passband is bounded on the left by a fourth protan stopband, and on the right by a fifth protan passband, the average transmission of the fourth protan stopband over a range of at least 20 nm is less than 10%, the average transmission of the fifth protan stopband over a range of at least 40 nm is less than 10%. In FIG. 13, the fourth and fifth protan stopbands are designated by p4 and p5, respectively.

Preferably, the spectral transmission profile of the filter for correcting severe protanomaly also includes an additional, ninth protan passband, having an approximately flat top, the lower band boundary of the ninth protan passband is 20 to 40 nm from the upper limit of the FWHM of the eighth protan passband. The average transmission within the wavelength range of the FWHM is preferably at least 80%. In FIG. 13, the ninth protan passband is denoted by IX'.

A sixth protan stopband is formed between the eighth and ninth protan passbands, having an average transmission of less than 25%, preferably less than 10%, over a range of at least 10 nm.

In the case of the colour filter for correcting severe protanomaly, similarly to the case of mild to moderate protanomaly-correcting colour filter, the inventors identified features the physical-biological effects of which improve the ability of the subject with severe protanomaly to distinguish colours (colour discrimination), and to recognize colours (colour identification). Only the differences compared to those described earlier will be discussed here. Since in the case of severe protanomaly (close to protanopia) the location P* of the maximum of the protos sensitivity curve is even more shifted in the direction of the location D of the maximum of the deuteros sensitivity curve (the two almost coincide), thus the effects described earlier are needed in a more intense form. Accordingly, the FWHM and the transmission of the seventh passband VII' serving to shift the protos sensitivity curve are smaller than shown in FIG. 12.

In the case of severe protanomaly, the tritos and protos sensitivity curves are also abnormally close to each other, which causes more frequent colour vision deficiency in the lower wavelength ranges, affecting the colours turquoise, blue, and purple. For this reason, the filter according to the invention has two separate fifth and sixth passbands V', VI' in the sensitivity range of the tritos receptor, which, according to the inventors' experience, results in improved discrimination and identification of turquoise, blue and purple colours.

The protos, which is shifted to the left is removed from the wavelength range resulting from the abnormal overlap of the deuteros and protos sensitivity curves and providing a faulty receptor signal by the second stopband p2.

The strongly left-shifted protos is displaced by the fifth stopband p5 from the wavelength range of the abnormal overlap of the deuteros and protos sensitivity curves which provides a faulty receptor signal. However, since the protos is shifted more to the left, the sixth stopband p6 following the eighth passband VIII' is also shifted to the left relative to the previously seen filter in order to better fulfil its signal amplifying effect.

In case of the preferred embodiments shown in FIGS. 12 and 13, during the design process, weights were applied that took greater account of the discrimination of green and orange colour samples from each other. The transmission of the third stopband p3 and the sixth stopband p6 will therefore be optimally below 10%. However, such a narrow band that blocks transmission so strongly compared to its environment is difficult to achieve with a thin film technology. The transmission curve of the filter shown in FIG. 13 does not achieve such blocking effect, but in practice, measurements have shown that in the case of severe protanomaly satisfactory colour vision experience can be provided with a stopband the average transmission of which remains below 25% over a range of at least 10 nm. However, by allowing more than 40 thin layers in production or using other technology, an average transmission of less than 10% can also be achieved in accordance with the value calculated for the design transmission curve.

These measures improve, at the same time, the ability to distinguish and identify colours for a person with severe protanomaly.

Although the above filters have been described as elements of a filter set, any of the filters shown are capable of correcting deuteranomaly or protanomaly on their own, thus the filters can also be used independently, and not just as elements of a filter set.

Various modifications to the above disclosed embodiments will be apparent to a person skilled in the art without departing from the scope of protection determined by the attached claims.

The invention claimed is:

1. The method of designing a colour filter for modifying human colour vision of a targeted eye having spectral sensitivity functions of L-cone, M-cone and S-cone colour-sensing receptors, characterised by providing a colour sample set having a plurality of colour samples, determining first and second reference opponent channel signals of ganglion cells of a reference eye produced in response to each colour sample of the colour sample set, determining from the first and second reference channel signals for each colour sample a reference colour point and a corresponding reference hue angle in a coordinate system wherein the first and second reference opponent channel signals of the reference colour point are measured along first and second coordinate axes of the coordinate system, respectively, and a corresponding reference hue angle is measured between the first coordinate axis and a straight line connecting the reference colour point with an origin of the coordinate system, providing a starting colour filter, having an arbitrary spectral transmission function $\tau_0(\lambda)$, calculating first and second modified opponent channel signals of ganglion cells of the targeted eye from spectral sensitivity functions of the targeted eye as modified by the starting colour filter for each colour sample of the colour sample set, determining from the first and second modified opponent channel signals for each colour sample a modified colour point and a corresponding modified hue angle in the coordinate system, and determining distances between the modified colour points in the coordinate system, determining the spectral transmission function of the colour filter by extreme value searching by modifying the spectral transmission function $\tau 0(\lambda)$ of the starting colour filter stepwise until reaching a colour filter having a spectral transmission function $\tau(\lambda)$ for which distances between modified colour points corresponding to the colour samples are maximal while at the same time the angular differences between modified hue angles of modified colour points and the reference hue angles of the reference colour points of corresponding colour samples are minimal.

2. The method according to claim 1, characterised by determining the reference channel signals on the basis of spectral sensitivity functions of L-cone, M-cone and S-cone colour-sensing receptors of the reference eye and of spectral luminance distributions of the colour samples.

3. The method according to claim 1, characterised by applying weighting factors to at least one distance of the modified colour points of the colour samples and the angular differences between the modified hue angles of the modified colour points and the reference hue angles of the reference colour points of the corresponding colour samples when performing the extreme value search.

4. The method according to claim 1, characterised by using red-green and blue-yellow opponent channel signals (CRG, CBY) and determining the hue angles as $$\alpha = \mathrm{arctg}\frac{y}{x}$$

wherein variable x corresponds to one of the channel signal values CRG, CBY, and variable y corresponds to the other one of the channel signal values CRG, CBY.

5. The method according to claim 1, characterised by using red-green and blue-yellow opponent channel signals ($C_{RG}$, $C_{BY}$) and determining the distance of a first modified colour point (A) and a second modified colour point (B) as $$d_{AB} = \sqrt{[C_{BY}(A) - C_{BY}(B)]^2 + [C_{RG}(A) - C_{RG}(B)]^2}$$

wherein $C_{RG}(A)$, $C_{BY}(A)$ are the opponent channel signals of the first colour point (A) and $C_{RG}(B)$, $C_{BY}(B)$ are the opponent channel signals of the second colour point (B).

6. The method according to claim 1, characterised by that the colour sample set comprises colour samples taken from the visible light wavelength range at every 1 to 20 nm, preferably at every 5 to 15 nm, even more preferably at every approximately 10 nm.

7. The method according to claim 1, characterised by that the colour sample set comprises the basic colours of a group consisting of a given computer monitor type, a given mobile phone type, a given tablet type, a given notebook type and a given television screen type.

8. The method according to claim 1, characterised by that the colour sample set consists of the red and green colours of a standard traffic light.

9. The method according to claim 1, characterised by that the colour sample set consists of colours of LED displays of control panels.

10. The method according to claim 1, characterised by that colour sample set consists of the colour signals used in transport selected from a group consisting of railway transport, air transport and water transport.

11. Colour filter for modifying human colour vision, characterised by that its spectral transmission function is determined with the design method according to claim 1.

12. The colour filter according to claim 11, characterised by that the colour sample set consists of colour samples taken from the visible light wavelength range at every 1 to 20 nm.

13. Colour filter set, characterised by having at least two colour filters having spectral transmission functions which are determined with the design method according to claim 1, and
the spectral transmission function of a first colour filter of the at least two colour filters is designed to modify the colour vision of a human eye with colour vision, the spectral sensitivity function of the L-cone colour sensing receptor of which is shifted by a value of 5 to 24 nm, preferably by a value of 10 to 20 nm in the direction of shorter wavelength light as compared to an eye with normal colour vision, while the spectral sensitivity functions of the M- and S-cone colour sensing receptors correspond to those of an eye with normal colour vision,
the spectral transmission function of a second colour filter of the at least two colour filters is designed to modify the colour vision of a human eye with colour vision, the spectral sensitivity function of the M-cone colour sensing receptor of which is shifted by a value of 5 to 24 nm, preferably by a value of 10 to 20 nm in the direction of longer wavelength light as compared to an eye with normal colour vision, while the spectral sensitivity functions of the L- and S-cone colour sensing receptors correspond to those of an eye with normal colour vision.

14. Colour filter set according to claim 13, characterised by that it contains
a third colour filter the spectral transmission function of which is designed to modify the colour vision of a human eye with colour vision, the spectral sensitivity function of the L-cone colour sensing receptor of which is shifted by 25 to 28 nm in the direction of shorter wavelength light, while the spectral sensitivity functions of the M- and S-cone colour sensing receptors correspond to those of an eye with normal colour vision, and
a fourth colour filter, the spectral transmission function of which is designed to modify the colour vision of a human eye with colour vision, the spectral sensitivity function of the M-cone colour sensing receptor of which is shifted by 25 to 28 nm in the direction of longer wavelength light, while the spectral sensitivity functions of the L- and S-cone colour sensing receptors correspond to those of an eye with normal colour vision.

15. Colour filter set for ameliorating human colour vision of subjects with colour vision deficiency, comprising at least one first colour filter for correcting deuteranomaly and at least one second colour filter for correcting protanomaly, characterised by that
a spectral transmission profile of the at least one first colour filter for correcting deuteranomaly comprises:
a first deutan passband having a full-width at half maximum (FWHM) of 30-60 nm, an approximately flat top and a centre wavelength between 420 to 460 nm,
a second deutan passband with an FWHM of 20 to 80 nm and a centre wavelength between 500 and 530 nm,
a third deutan passband with an approximately flat top and an FWHM of at least 120 nm, the lower limit of which is between 590 and 620 nm,
a first deutan stopband between the first and second deutan passbands with an average transmission of less than 20% over a range of at least 20 nm,
a second deutan stopband between the second and third deutan passbands the average transmission of which is less than 20%, preferably less than 10%, over a range of at least 20 nm;
a spectral transmission profile of the at least one second colour filter for correcting protanomaly comprises:
a first protan passband with an FWHM of 30 to 60 nm and a centre wavelength between 425 and 455 nm,
a second protan passband with an FWHM of 40 to 60 nm, and a transmission that increases in average in the direction of small wavelengths, the lower band boundary of which is between 495 and 515 nm,
a third protan passband with a lower band boundary between 590 and 620 nm and an upper band boundary between 645 and 670 nm, a first protan stopband between the first and second protan passbands with an average transmission of less than 20% over a range of at least 20 nm, a second protan stopband between the second and third protan passbands, having an average transmission of less than 20%, preferably less than 10%, over a range of at least 20 nm.

16. The colour filter set according to claim 15, characterised by that the spectral transmission profile of the at least one second colour filter for correcting protanomaly further comprises:

a fourth protan passband with an approximately flat top, the lower band boundary of which is 20 to 40 nm from an upper bound boundary of the third protan passband, a third protan stopband between the third and fourth protan passbands with an average transmission of less than 20% over a range of at least 10 nm.

17. The colour filter set according to claim 15, characterised by comprising a third colour filter for correcting deuteranomaly and a fourth colour filter for correcting protanomaly, and a spectral transmission profile of the third colour filter for correcting deuteranomaly comprises:

a fourth deutan passband having an FWHM of at least 10 nm and a peak between 410 and 425 nm, a fifth deutan passband having an FWHM of 20 to 60 nm and a centre wavelength between 460 and 490 nm, a sixth deutan passband with an approximately flat top and an FWHM of at least 120 nm, with a lower band boundary between 590 and 610 nm, a third deutan stopband between the fourth and fifth deutan passbands with an average transmission of less than 25% over a range of at least 20 nm, a fourth deutan stopband between the fifth and sixth deutan passbands, having an average transmission of less than 20%, preferably less than 10% over a region of at least 30 nm;

a spectral transmission profile of the fourth colour filter for correcting protanomaly comprises:

a fifth and sixth protan passband between 395 and 470 nm with an average transmission greater than 20%, a seventh protan passband with an FWHM of 20 to 40 nm a transmission of which increases in average in a direction of small wavelengths, a lower band boundary of the seventh protan passband being between 500 and 515 nm and having an average transmission of less than 20%, an eighth protan passband with an FWHM of 20 to 70 nm, a lower band boundary of the eighth protan passband being between 590 and 615 nm and having an average transmission of at least 80%, the seventh protan passband being bound on the left by a fourth protan stopband, on the right by a fifth protan stopband, an average transmission of the fourth protan stopband being less than 10% over a range of at least 20 nm, an average transmission of the fifth protan stopband being less than 10% over a range of at least 40 nm.

18. The colour filter set according to claim 17, characterised by that the spectral transmission profile of the fourth colour filter for correcting protanomaly further comprises:

a ninth protan passband having an approximately flat top, a lower band boundary of the ninth protan passband being 20 to 40 nm from the upper band boundary of the eighth protan passband, a sixth protan stopband between the eighth and ninth protan passbands, having an average transmission of less than 25%, preferably less than 10%, over a range of at least 10 nm.

* * * * *

UNITED STATES PATENT AND TRADEMARK OFFICE
CERTIFICATE OF CORRECTION

| | | |
|---|---|---|
| PATENT NO. | : 12,326,618 B2 | Page 1 of 1 |
| APPLICATION NO. | : 17/765952 | |
| DATED | : June 10, 2025 | |
| INVENTOR(S) | : György Ábrahám et al. | |

It is certified that error appears in the above-identified patent and that said Letters Patent is hereby corrected as shown below:

On the Title Page

Under (30) "Foreign Priority Data,":
Delete "Dec. 19, 2019 (HU) ............................... 19217955.4"
And insert -- Dec. 19, 2019 (EP) ................................ 19217955.4 --

Signed and Sealed this
Twenty-second Day of July, 2025

Coke Morgan Stewart
*Acting Director of the United States Patent and Trademark Office*